(12) United States Patent
Brink et al.

(10) Patent No.: US 10,315,031 B2
(45) Date of Patent: *Jun. 11, 2019

(54) ELECTRICAL STIMULATION TO INHIBIT BLADDER AND/OR BOWEL CONTRACTION

(71) Applicant: Medtronic, Inc., Minneapolis, MN (US)

(72) Inventors: Thaddeus S. Brink, St. Paul, MN (US); Xin Su, Plymouth, MN (US); Dwight E. Nelson, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/967,329

(22) Filed: Apr. 30, 2018

(65) Prior Publication Data

US 2018/0243559 A1    Aug. 30, 2018

Related U.S. Application Data

(63) Continuation of application No. 14/946,431, filed on Nov. 19, 2015, now Pat. No. 9,956,404.

(60) Provisional application No. 62/082,003, filed on Nov. 19, 2014.

(51) Int. Cl.
    *A61N 1/36* (2006.01)

(52) U.S. Cl.
    CPC ................... *A61N 1/36007* (2013.01)

(58) Field of Classification Search
    CPC .................................. A61N 1/36007
    USPC ......................................... 607/41
    See application file for complete search history.

(56) References Cited

U.S. PATENT DOCUMENTS

| | | |
|---|---|---|
| 5,603,726 A | 2/1997 | Schulman et al. |
| 5,800,465 A | 9/1998 | Thompson et al. |
| 6,289,247 B1 | 9/2001 | Faltys et al. |
| 6,314,325 B1 | 11/2001 | Fitz |

(Continued)

FOREIGN PATENT DOCUMENTS

| | | |
|---|---|---|
| CN | 107050645 A | 8/2017 |
| EP | 2396072 B1 | 3/2013 |

(Continued)

OTHER PUBLICATIONS

"St. Jude's Prodigy Neurostimulator with Burst Technology," Medgadget, Mar. 20, 2014, 4 pp.

(Continued)

*Primary Examiner* — Nadia A Mahmood
(74) *Attorney, Agent, or Firm* — Shumaker & Sieffert, P.A.

(57) ABSTRACT

In one example, a method including generating electrical stimulation therapy with a frequency of approximately 500 hertz or greater, and controlling delivery of the electrical stimulation therapy to a patient via a medical device between at least one of contractions of a bladder or contractions of a bowel of a patient, wherein the electrical stimulation therapy comprises electrical stimulation therapy configured to inhibit contraction of the bladder when the electrical stimulation is delivered between the contractions of the bladder, wherein the electrical stimulation therapy comprises electrical stimulation therapy configured to inhibit contraction of the bowel when the electrical stimulation is delivered between the contractions of the bowel, and wherein at least one of the generating and controlling is performed via one or more processors.

20 Claims, 9 Drawing Sheets

(56) References Cited

U.S. PATENT DOCUMENTS

| | | | |
|---|---|---|---|
| 6,421,566 | B1 | 7/2002 | Holsheimer |
| 6,505,078 | B1 | 1/2003 | King et al. |
| 6,675,046 | B2 | 1/2004 | Holsheimer |
| 6,850,802 | B2 | 2/2005 | Holsheimer |
| 6,988,006 | B2 | 1/2006 | King et al. |
| 7,333,858 | B2 | 2/2008 | Killian et al. |
| 7,577,480 | B2 | 8/2009 | Zeijlemaker |
| 7,657,318 | B2 | 2/2010 | King et al. |
| 7,689,289 | B2 | 3/2010 | King |
| 7,742,810 | B2 | 6/2010 | Moffitt et al. |
| 8,359,103 | B2 | 6/2013 | Alataris et al. |
| 8,504,150 | B2 | 8/2013 | Skelton |
| 8,620,441 | B2 | 12/2013 | Greenberg et al. |
| 8,694,108 | B2 | 4/2014 | Alataris et al. |
| 8,708,934 | B2 | 4/2014 | Skelton et al. |
| 8,712,533 | B2 | 4/2014 | Alataris et al. |
| 8,712,534 | B2 | 4/2014 | Wei |
| 9,002,460 | B2 | 4/2015 | Parker |
| 9,138,582 | B2 | 9/2015 | Doan et al. |
| 9,155,892 | B2 | 10/2015 | Parker et al. |
| 9,339,655 | B2 | 5/2016 | Carbunaru |
| 9,381,356 | B2 | 7/2016 | Parker et al. |
| 9,386,934 | B2 | 7/2016 | Parker et al. |
| 2004/0267333 | A1 | 12/2004 | Kronberg |
| 2007/0067004 | A1 | 3/2007 | Boveja et al. |
| 2009/0036945 | A1 | 2/2009 | Chancellor et al. |
| 2009/0222053 | A1 | 9/2009 | Gaunt et al. |
| 2011/0054570 | A1 | 3/2011 | Lane |
| 2011/0071589 | A1 | 3/2011 | Starkebaum et al. |
| 2011/0125223 | A1 | 5/2011 | Carbunaru et al. |
| 2011/0282412 | A1 | 11/2011 | Glukhovsky et al. |
| 2012/0130444 | A1 | 5/2012 | Wei et al. |
| 2012/0155188 | A1 | 6/2012 | Buettner et al. |
| 2012/0296389 | A1 | 11/2012 | Fang et al. |
| 2013/0110194 | A1 | 5/2013 | Wei |
| 2013/0208390 | A1 | 8/2013 | Singh et al. |
| 2013/0268021 | A1 | 10/2013 | Moffitt |
| 2013/0289664 | A1 | 10/2013 | Johanek |
| 2014/0005753 | A1 | 1/2014 | Carbunaru |
| 2014/0025146 | A1 | 1/2014 | Alataris et al. |
| 2014/0031896 | A1 | 1/2014 | Alataris et al. |
| 2014/0031905 | A1 | 1/2014 | Irazoqui et al. |
| 2014/0074189 | A1 | 3/2014 | Moffitt |
| 2014/0142656 | A1 | 5/2014 | Alataris et al. |
| 2014/0142673 | A1 | 5/2014 | Alataris et al. |
| 2014/0243924 | A1 | 8/2014 | Zhu et al. |
| 2014/0296936 | A1 | 10/2014 | Alataris et al. |
| 2014/0371813 | A1 | 12/2014 | King et al. |
| 2014/0379043 | A1 | 12/2014 | Howard |
| 2015/0127062 | A1 | 5/2015 | Holley et al. |
| 2015/0179177 | A1 | 6/2015 | Nagao |
| 2016/0030741 | A1 | 2/2016 | Wei et al. |
| 2016/0136420 | A1 | 5/2016 | Brink et al. |
| 2017/0209695 | A1 | 7/2017 | Solomon |
| 2018/0154144 | A1 | 6/2018 | Brink et al. |

FOREIGN PATENT DOCUMENTS

| | | |
|---|---|---|
| WO | 2002009808 A1 | 2/2002 |
| WO | 2010058178 A1 | 5/2010 |
| WO | 2010123704 A2 | 10/2010 |
| WO | 2011156286 A2 | 12/2011 |
| WO | 2015179177 A1 | 11/2015 |
| WO | 2015179281 A1 | 11/2015 |
| WO | 2017106503 A1 | 6/2017 |

OTHER PUBLICATIONS

Abejon et al., "Back pain coverage with spinal cord stimulation: A different treatment for each patient," International Neuromodulation Society. Jun. 10, 2015; 567, Abstract Only, 1 pp.

Abeloos, et al., "High density stimulation as an alternative to uncomfortable cervical tonic spinal cord stimulation: case report," International Neuromodulation Society 12th World Congress, Jun. 11-15, 2015, Abstract Only, 1 pp.

Bhadra et al., "High frequency electrical conduction block of the pudendal nerve," Journal of Neural Eng., IOP Publishing LTD, published Jun. 3, 2006,14 pp.

Boger et al., "Bladder Voiding by Combined High Frequency Electrical Pudendal Nerve Block and Sacral Root Stimulation," Neurourology and Urodynamics, Wiley InterScience, vol. 27, Issue 5, Jul. 2, 2008, 6 pp.

Breel, et al., "High Density Stimulation: A novel programming paradigm for the treatment of chronic pain," International Neuromodulation Society (INS) 12th World Congress; Jun. 9, 2015, Abstract Only, 1 pp.

Cuellar MD et al., "Effect of high-frequency alternating current on spinal afferent nociceptive transmission," Neuromodulation: Technology at the Neural Interface; Jul.-Aug. 2013;16(4): pp. 318-327.

Cui et al., "Spinal cord stimulation attenuates augmented dorsal horn release of excitatory amino acids in mononeuropathy via a GABAergic mechanism," Pain 73, Oct. 1997, pp. 87-95.

Cui, et al., "Effect of spinal cord stimulation on tactile hypersensitivity in mononeuropathic rats is potentiated by simultaneous GABA(B) and adenosine receptor activation," Neuroscience Letters 247: Apr. 1998; pp. 183-186.

De Ridder, et al., "Burst spinal cord stimulation for limb and back pain," World neurosurgery, Nov. 2013; 80 (5):642-649 e641.

De Ridder, et al., "Burst spinal cord stimulation: toward paresthesia-free pain suppression," Neurosurgery. May 2010; 66(5): 986-990.

Downey, "Asynchronous Neuromuscular Electrical Stimulation," University of Florida, 2015, accessed on Jul. 18, 2016, 107 pp.

Duyvendak, MD, et al., "High density stimulation: a novel programming paradigm for the treatment of chronic back and leg pain," Abstracts, International Neuromodulation Society 12th World Congress: Jun. 11-15, 2015, 1 pp.

Gao et al., "Effects of spinal cord stimulation with "standard clinical" and higher frequencies on peripheral blood flow in rats," Brain Res. Feb. 8, 2010;1313: pp. 53-61.

Grider, et al., "High Frequency (1000 Hz) Stimulation Using Commercially Available Implantable Pulse Generator," North American Neuromodulation Society. Dec. 2013, Abstract Only, 2 pp.

Guan et al., "Spinal Cord Stimulation: Neurophysiological and Neurochemical Mechanisms of Action" Curr Pain Headache Rep DOI 10,1007s11916-014-0260-4, Mar. 2012, pp. 217-225.

Guan et al., "Spinal cord stimulation-induced analgesia: electrical stimulation of dorsal column and dorsal roots attenuates dorsal horn neuronal excitability in neuropathic rats," Anesthesiology. Dec. 2010;113(6): pp. 1392-1405.

Holsheimer, "Computer modelling of spinal cord stimulation and its contribution to therapeutic efficacy," Spinal Cord Aug. 1998, 36: pp. 531-540.

Hubscher, et al., "Convergence and cross talk in urogenital neural circuitries," J. Neurophysiol 110: 1997-2005, first published Aug. 7, 2013, 9 pp.

Hunt SP, Mantyh PW. The molecular dynamics of pain control. Nat Rev Neurosci. Feb. 2001;2(2):83-91.

Kemler, et al., "Spinal cord stimulation in patients with chronic reflex sympathetic dystrophy," N Engl J Med, Aug. 31, 2000; 343(9):618-624.

Kilgore, PhD, et al., "Reversible Nerve Conduction Block Using Kilohertz Frequency Alternating Current," Neuromodulation. Aug. 2013, pp. 242-255.

Kumar, et al., "Spinal cord stimulation versus conventional medical management for neuropathic pain: a multicentre randomised controlled trial in patients with failed back surgery syndrome," Pain Jul. 2007; 132(1-2): 179-188.

Likar et al., "High density spinal cord stimulation: a multi-center experience," Abstracts, International Neuromodulation Society 12th World Congress; Jun. 11-15, 2015, 1 pp.

Maeda, et al., "Increased c-fos immunoreactivity in the spinal cord and brain following spinal cord stimulation is frequency-dependent," Brain Res. Mar. 9, 2009;1259: pp. 40-50.

Maeda, et al., "Low frequencies, but not high frequencies of bi-polar spinal cord stimulation reduce cutaneous and muscle hyperalgesia induced by nerve injury," Pain; Feb. 2008; 138(1): pp. 143-152.

(56) References Cited

OTHER PUBLICATIONS

Maggi, et al., "Effect of urethane anesthesia on the micturition reflex in capsaicin-treated rats." Journal of the Autonomic Nervous System, Jan. 1990, 30(3): 247-251.
North M.D. et al., "Spinal cord stimulation versus repeated lumbosacral spine surgery for chronic pain: a randomized, controlled trial," Neurosurgery, Jan. 2005; 56(1): 98-106; discussion 106-107.
North, et al., "Clinical outcomes of 1 kHz subperception spinal cord stimulation (SCS): Results of a prospective randomized controlled crossover trial," Abstracts, International Neuromodulation Society, Jun. 2015, 1 pp.
Ranck Jr., et al., "Which elements are excited in electrical stimulation of mammalian central nervous system: a review," Brain Res. Nov. 21, 1975; 98(3): pp. 417-440.
Replogle, MD., et al., "Case Series Comparing Moderate (1000 Hz) Versus Conventional Frequency Stimulation During Spinal Cord Stimulator Trials," North American Neuromodulation Society. 2014, 1 pp. Applicant points out in accordance with MPEP 609.04(a) that the 2014 year of publication is sufficiently earlier than the effective U.S. filing date of the present application, and any foreign priority date that the particular month of publication is not in issue.
Sato, et al., "Spinal cord stimulation reduces hypersensitivity through activation of opioid receptors in a frequency-dependent manner," Eur J Pain. Apr. 17, 2012 (4): pp. 551-561.
Schu et al., "A prospective, randomised, double-blind, placebo-controlled study to examine the effectiveness of burst spinal cord stimulation patterns for the treatment of failed back surgery syndrome," Neuromodulation. Apr. 2014; 17 (5): pp. 443-450.
Shechter et al., "Conventional and kilohertz-frequency spinal cord stimulation produces intensity- and frequency-dependent inhibition of mechnical hypersensitivity in a rat model of neuropathic pain," Anesthesiology, Aug. 2013; 119(2): pp. 422-432.
Sluka, et al., "High-frequency, but not low-frequency, transcutaneous electrical nerve stimulation reduces aspartate and glutamate release in the spinal cord dorsal horn," J Neurochem. Oct. 17, 2005; 95(6); pp. 1794-1801.
Smith, et al., "Successful use of high-frequency spinal cord stimulation following traditional treatment failure," Stereotact Funct Neurosurg. Apr. 2015; 93(3): pp. 190-193.
Snellings et al., "Effects of stimulation site and stimulation parameters on baldder inhibition by electrical nerve stimulation," BJU International, published Aug. 9, 2011, pp. 136-143.
Song, et al., "Efficacy of kilohertz-frequency and conventional spinal cord stimulation in rat models of different pain conditions," Neuromodulation Jan. 2014; 17(3): pp. 226-234.
Sweet et al., "High Frequency vs. Burst Stimulation Patterns for Dorsal Column Stimulation: The Importance of Charge," American Association of Neurological Surgeons, Abstract, Apr. 4, 2014, 2 pp.
U.S. Appl. No. 15/623,141, by Nathan A. Torgerson, filed Jun. 14, 2017.
Walter et al., "Inhibiting the hyperreflexic Bladder with Electrical Stimulation in a Spinal Animal Model," Neurourology and Urodynamics, Wiley-Liss, Inc. Oct. 19, 1992, 12 pp.
Wille, MD, et al., "Altering Conventional to High Density Spinal Cord Stimulation: An Energy Dose-Response Relationship in Neuropathic Pain Therapy," Neuromodulation: Technology at the Neural Interface, Aug. 2016, 9 pp.
Woock, et al., "Activation and inhibition of the micturition reflex by penile afferents in the cat," Am J. Physiol Regul Intergre Comp Physiol, published Apr. 23, 2008, pp. R1880-R1889.
Youn et al., "The Effect of High Frequency Stimulation on Sensory Thresholds in Chronic Pain Patients," North American Neuromodulation Society. 2014, 1 pp. Applicant points out in accordance with MPEP 609.04(a) that the 2014 year of publication is sufficiently earlier than the effective U.S. filing date of the present application, and any foreign priority date that the particular month of publication is not in issue.
Prosecution History from U.S. Appl. No. 14/946,431, dated Mar. 22, 2017 through Dec. 22, 2017, 34 pp.
Prosecution History from U.S. Appl. No. 15/831,986, dated Dec. 12, 2017 through Apr. 2, 2018, 60 pp.

ELECTRICAL STIMULATION TO INHIBIT BLADDER AND/OR BOWEL CONTRACTION

This application is a continuation of U.S. patent application Ser. No. 14/946,431, filed Nov. 19, 2015, which claims the benefit of U.S. Provisional Patent Application No. 62/082,003, filed Nov. 19, 2014. The entire content of each of these applications is incorporated herein by reference.

TECHNICAL FIELD

The disclosure relates to medical devices and, more particularly, to medical devices that may be configured to deliver electrical stimulation.

BACKGROUND

Urinary and fecal incontinence (e.g., an inability to control bladder and bowel function, respectively) are problems that afflict people of all ages, genders, and races. Various muscles, nerves, organs and conduits within the pelvic floor cooperate to collect, store and release bladder and bowel contents. A variety of disorders may compromise urinary tract and bowel performance, and contribute to incontinence. Many of the disorders may be associated with aging, injury, or illness.

Urinary incontinence, such as, urgency incontinence, may originate from disorders of portions of the peripheral or central nervous system which control the bladder micturition reflex. Nerve disorders may also lead to overactive bladder activities and/or may prevent proper triggering and operation of the bladder. Furthermore, urinary incontinence may also result from improper communication between the nervous system and the urethra.

SUMMARY

Devices, systems, and techniques for managing incontinence (bladder incontinence and/or fecal incontinence) of a patient and/or other patient conditions using electrical stimulation are described in this disclosure. In some examples, a medical device is configured to deliver a high frequency (HF) electrical stimulation to a patient for a period of time between the contractions of the bladder (e.g., in the case of urinary incontinence) or between contractions of the bowel (e.g., in the case of fecal incontinence). The HF electrical stimulation may have a frequency of approximately 500 hertz (Hz) or greater, such as, e.g., approximately 1 kilohertz (kHz) or greater or between approximately 1 kHz and approximately 100 kHz. The delivery of such HF electrical stimulation to the patient may inhibit bladder contraction of a patient between bladder contractions, e.g., to manage urinary incontinence. For example, following a bladder contraction, the HF stimulation may prevent the bladder from contracting again while the HF stimulation is being delivered. In a similar fashion, the delivery of such HF electrical stimulation to the patient may inhibit bowel contraction of a patient between bowel contractions, e.g., to manage fecal incontinence.

In one example, the disclosure is directed to a method comprising generating electrical stimulation therapy with a frequency of approximately 500 hertz or greater; and controlling delivery of the electrical stimulation therapy to a patient via a medical device between at least one of contractions of a bladder or contractions of a bowel of a patient, wherein the electrical stimulation therapy comprises electrical stimulation therapy configured to inhibit contraction of the bladder when the electrical stimulation is delivered between the contractions of the bladder, wherein the electrical stimulation therapy comprises electrical stimulation therapy configured to inhibit contraction of the bowel when the electrical stimulation is delivered between the contractions of the bowel, and wherein at least one of the generating and controlling is performed via one or more processors.

In another example, the disclosure is directed to a system comprising a therapy module configured to deliver electrical stimulation therapy to a patient; and a processor configured to control delivery of the electrical stimulation therapy to the patient via the therapy module between at least one of contractions of a bladder or contractions of a bowel of a patient, wherein the electrical stimulation therapy exhibits a frequency of approximately 500 hertz or greater, wherein the electrical stimulation therapy comprises electrical stimulation therapy configured to inhibit contraction of the bladder when the electrical stimulation is delivered between the contractions of the bladder, wherein the electrical stimulation therapy comprises electrical stimulation therapy configured to inhibit contraction of the bowel when the electrical stimulation is delivered between the contractions of the bowel.

In another example, the disclosure is directed to a system comprising means for generating electrical stimulation therapy with a frequency of approximately 500 hertz or greater; and means for controlling delivery of the electrical stimulation therapy to a patient via a medical device between at least one of contractions of a bladder or contractions of a bowel of a patient, wherein the electrical stimulation therapy comprises electrical stimulation therapy configured to inhibit contraction of the bladder when the electrical stimulation therapy is delivered between the contractions of the bladder, and wherein the electrical stimulation therapy comprises electrical stimulation therapy configured to inhibit contraction of the bowel when the electrical stimulation is delivered between the contractions of the bowel.

In another example, the disclosure is directed to a non-transitory computer-readable storage medium comprising instructions that, when executed by at least one processor, cause the at least one processor to control delivery of the electrical stimulation therapy with a frequency of approximately 500 hertz or greater to a patient via a medical device between at least one of contractions of a bladder or contractions of a bowel of a patient, wherein the electrical stimulation therapy comprises electrical stimulation therapy configured to inhibit contraction of the bladder when the electrical stimulation therapy is delivered between the contractions of the bladder, wherein the electrical stimulation therapy comprises electrical stimulation therapy configured to inhibit contraction of the bowel when the electrical stimulation therapy is delivered between the contractions of the bowel.

The details of one or more aspects of the disclosure are set forth in the accompanying drawings and the description below.

DETAILED DESCRIPTION

Figure 1:
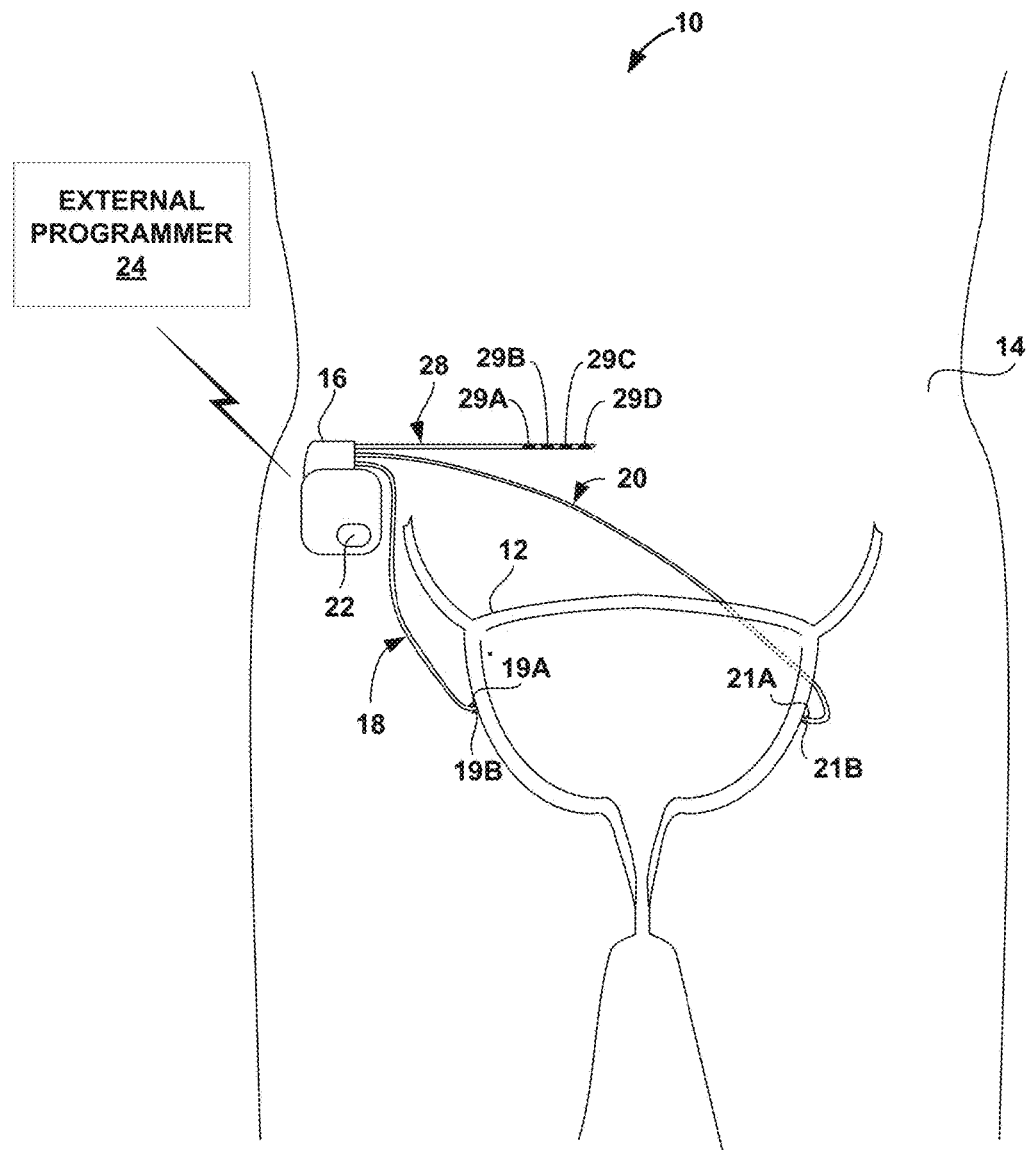
FIG. 1 is a conceptual diagram illustrating an example therapy system that delivers stimulation therapy to a patient to manage a patient condition such as, e.g., incontinence.

As described above, devices, systems, and techniques for managing incontinence (bladder incontinence and/or fecal incontinence) of a patient and/or other patient conditions using electrical stimulation are described in this disclosure. In some examples, a medical device is configured to deliver a HF electrical stimulation to a patient for a period of time between the contractions of the bladder (e.g., in the case of urinary incontinence) or between contractions of the bowel (e.g., in the case of fecal incontinence). The HF electrical stimulation may have a frequency of approximately 500 Hz or greater, such as, e.g., approximately 600 Hz or greater, approximately 700 Hz or greater, approximately 800 Hz or greater, approximately 900 Hz or greater, approximately 1 kHz, or greater or between approximately 1 kHz and approximately 100 kHz. The delivery of such HF electrical stimulation to the patient may inhibit bladder contraction of a patient between bladder contractions, e.g., to manage urinary incontinence. For example, following a bladder contraction, the HF stimulation may prevent the bladder from contracting again while the HF stimulation is being delivered. In a similar fashion, the delivery of such HF electrical stimulation to the patient may inhibit bowel contraction of a patient between bowel contractions, e.g., to manage fecal incontinence.

Electrical stimulation therapy may include delivery of electrical stimulation of peripheral nerves (e.g., sacral, pudendal, dorsal genital, tibial nerve, and branches of any of the aforementioned nerves) via a medical device. Such electrical stimulation may be used to modify pelvic function to treat various patient conditions (e.g., urinary incontinence and fecal incontinence). Although the present disclosure describes application of electrical stimulation using an IMD, the devices, systems, and techniques of the present disclosure may also be implemented in an external medical device that applies electrical stimulation via implanted or external electrodes.

It is has been determined that, in some cases, the delivery of relatively high frequency stimulation (e.g., approximately 500 Hz or greater, such as, e.g., approximately 1 kHz or greater) may inhibit contractions of the bladder and/or bowel of a patient. For example, a medical device may deliver HF stimulation to a patient following a bladder or bowel contraction (e.g., during a voiding event), such that stimulation results in the inhibition of bladder or bowel contractions, respectively, in the patient. Using such a mechanism, a medical device may deliver such HF stimulation to treat one or more patient conditions associated with undesirable bladder contractions, e.g., such as those contractions associated with involuntary voiding of the bladder or bowel of a patient and/or those contractions associated with urge incontinence.

Although examples of the disclosure are primarily described with regard to managing incontinence, in other examples, the HF stimulation may be delivered to a patient to manage other patient conditions by inhibiting contractions of the bladder and/or bowel, such as, e.g., overactive bladder or bowel, irritable bowel, pelvic pain, bowel pain, bladder pain, and the like.

Moreover, for ease of description, examples of the disclosure are primarily described with regard to delivering HF stimulation to inhibit bladder contraction, e.g., in a manner that treats a patient bladder condition such as urinary incontinence, including involuntary urinary voiding and urge incontinence, and bladder pain. However, examples are not limited as such. Other examples may include delivering HF stimulation to inhibit bowel contraction, e.g., in a manner that treats a bowel condition such as fecal incontinence and irritable bowel.

As described herein, a medical device may deliver HF stimulation to a patient between contractions of the bladder or bowel to inhibit bladder contraction or bowel contraction, respectively, of the patient. Contraction may refer to muscle contractions within the bladder or bowel. In the case of the bladder, contraction may include contraction of the detrusor muscle or other muscle in the bladder of a patient. Such bladder contraction may result in a physiologically significant event, such as, e.g., the voiding of urine from the bladder (either voluntary or involuntary), or urge incontinence. Bladder contraction may include reflex contraction, unwanted or pathological bladder contraction including both voiding and non-voiding contractions, such as, contractions causing urge incontinence. In the case of the bowel of a patient, bowel contraction may include bowel contraction that results in fecal voiding, either on a voluntary or involuntary basis.

The delivery of HF stimulation may inhibit bladder or bowel contraction by substantially blocking all muscle contraction of the bladder or bowel, respectfully or at least prevent the bladder or bowel from contracting in any physiologically significant manner e.g., contracting in a manner associated with the patient condition being treated. For example, in the case of delivery of HF stimulation of the bladder, a medical device may deliver HF electrical stimulation that inhibits bladder contraction by substantially blocking all muscle contraction of the bladder or at least prevent the bladder from contracting in a manner that results in voiding of urine from the bladder or resulting in urge incontinence. As another example, in the case of delivery of HF stimulation to the bowel, a medical device may deliver HF electrical stimulation that inhibits bowel contraction by substantially blocking all muscle contraction of the bowel or at least prevents the bladder from contracting in a manner that results in fecal voiding from the bowel. In some examples, the HF stimulation delivered to the patient may inhibit bladder and/or bowel contraction by modulating nerve signals including, e.g., blocking or inducing nerve signals. In some examples, the HF stimulation delivered to the patient to inhibit bladder contraction may define an intensity below a motor threshold of the stimulated bladder site, e.g., such that the stimulation does not result in a muscle evoked potential.

In some examples, following the contraction of the bladder (e.g., a contraction resulting in a voluntary or involuntary voiding event), a medical device may deliver HF stimulation to block the occurrence of a subsequent bladder contraction in the patient, such as, e.g., those contractions that result in voiding of the bladder or urge incontinence. The medical device may deliver the HF electrical stimulation to the patient to inhibit bladder contraction for period of time (e.g., on the order of seconds, minutes, or hours), e.g., to prevent the occurrence of undesired or pathological bladder contractions. The delivery of HF stimulation may be maintained until the occurrence of a bladder contraction is no longer undesired, e.g., once the bladder has reached some threshold fill level at which urinary voiding in no longer undesirable. Once the bladder contractions are no longer inhibited by the HF stimulation, the bladder of the patient may contract, e.g., resulting in the voiding of the bladder. In some examples, the contraction of the bladder may no longer be inhibited by the HF stimulation substantially immediately following termination of HF stimulation delivery. In other examples, bladder contractions may continue to be inhibited for some period of time even after the delivery of HF stimulation has been terminated. In some examples, by delivering HF stimulation between contractions of the bladder, a medical device may deliver HF stimulation to inhibit bladder contraction at a time when the bladder in not contracting or not contracting in any physiologically significant manner e.g., contracting in a manner associated with the patient condition being treated, rather than delivering the HF stimulation during a bladder contraction.

In some examples, an IMD may be configured to control delivery of HF stimulation to a patient to inhibit bladder contraction based on patient input. Patient input may include data received by the IMD from a patient programmer that indicates, for example, an amount of fluid intake by the patient, an urge felt by the patient, a leakage incident experienced by the patient, an imminent voiding event predicted by the patient, an occurrence of an involuntary voiding event or an occurrence of a voluntary voiding event undertaken by the patient.

Additionally or alternatively, an IMD may be configured to control delivery of HF stimulation to a patient to inhibit bladder contraction based on sensor data. The sensor data may be indicative of, for example, the occurrence of a bladder contraction resulting in a voiding event or urge incontinence. Bladder contraction frequency may be determined based on signals received from any suitable sensor or device. For example, bladder contraction may be determined using a sensor that indicates bladder impedance, bladder pressure, pudendal or sacral afferent nerve signals, external urinary sphincter electromyogram (EMG), motion (e.g., accelerometer signals), or any combination thereof. Based on the sensor data, the IMD may deliver HF stimulation to a patient to inhibit bladder contraction, e.g., prior to the occurrence of a directly subsequent bladder contraction.

In some examples, the HF stimulation may be delivered in combination with a lower frequency stimulation (e.g., stimulation with a frequency between approximately 1 Hz and approximately 50 Hz) to a patient. For example, the lower frequency electrical stimulation may be delivered on a substantially continuous basis with one or more periods of HF stimulation in cases in which the lower frequency stimulation is delivered to a different target site than the HF stimulation. The periods of HF stimulation may be delivered, e.g., on a random, timed, and/or physiomarker-linked basis. Additionally or alternatively, the period of HF stimulation may be delivered based on patient input. In other examples, the HF stimulation may be interleaved with the lower frequency stimulation.

FIG. 1 is a conceptual diagram illustrating an example therapy system 10 that delivers electrical stimulation therapy to a patient 14 to manage an urgency and/or urinary incontinence disorder of patient 14. Therapy system 10 includes an implantable medical device (IMD) 16, which is coupled to leads 18, 20, and 28, sensor 22, and external programmer 24. IMD 16 generally operates as a therapy device that delivers electrical stimulation to, for example, a tissue site proximate a pelvic floor nerve, a pelvic floor muscle, the urinary sphincter, or other pelvic floor targets. Pelvic floor nerves include peripheral nerves such as sacral nerves, pudendal nerves and associated branches, and dorsal genital nerves. In some examples, IMD 16 delivers the electrical stimulation therapy to a sacral nerve of patient 14 to inhibit bladder contractions.

IMD 16 provides electrical stimulation therapy to patient 14 by generating and delivering electrical stimulation signals to a target therapy site by lead 28 and, more particularly, via electrodes 29A-29D (collectively referred to as "electrodes 29") disposed proximate to a distal end of lead 28. For example, IMD 16 may deliver HF stimulation to patient 14 to inhibit bladder contraction following a bladder contraction, e.g., a contraction associated with a voiding event. In some examples, IMD 16 may delivery the HF stimulation to patient 14 based on, e.g., sensor data and/or patient input. As one example, IMD 16 may detect a bladder contraction based on sensor data and then deliver HF stimulation based on the detected bladder contraction. As another example, patient 14 may use external programmer 24 to provide patient input to IMD 16, e.g., indicating an increased probability of unintentional voiding, and IMD 16 may deliver the HF stimulation to patient 14 to inhibit bladder contraction based on the patient input.

IMD 16 may be surgically implanted in patient 14 at any suitable location within patient 14, such as near the pelvis. In some examples, the implantation site may be a subcutaneous location in the side of the lower abdomen or the side of the lower back or upper buttocks. IMD 16 has a biocompatible housing, which may be formed from titanium, stainless steel, a liquid crystal polymer, or the like. The proximal ends of leads 18, 20, and 28 are both electrically and mechanically coupled to IMD 16 either directly or indirectly, e.g., via a respective lead extension. Electrical conductors disposed within the lead bodies of leads 18, 20, and 28 electrically connect sense electrodes (not shown) and stimulation electrodes, such as electrodes 29, to a therapy delivery module (e.g., a stimulation generator) within IMD 16. In the example of FIG. 1, leads 18 and 20 carry electrodes 19A, 19B (collectively referred to as "electrodes 19") and electrodes 21A, 21B (collectively referred to as "electrodes 21"), respectively. As described in a further detail below, electrodes 19 and 21 may be positioned for sensing an impedance of bladder 12, which may decrease as the volume of urine within bladder 12 increases.

One or more medical leads, e.g., leads 18, 20, and 28, may be connected to IMD 16 and surgically or percutaneously tunneled to place one or more electrodes carried by a distal end of the respective lead at a desired pelvic nerve or muscle site, e.g., one of the previously listed target therapy sites such as a sacral or pudendal nerve. In FIG. 1, leads 18 and 20 are placed proximate to an exterior surface of the wall of bladder 12 at first and second locations, respectively. Electrodes 29 of the common lead 28 may deliver stimulation to the same or different nerves. In other examples of therapy system 10, IMD 16 may be coupled to more than one lead that includes electrodes for delivery of electrical stimulation to different stimulation sites within patient 14, e.g., to target different nerves.

In the example shown in FIG. 1, leads 18, 20, 28 are cylindrical. Electrodes 19, 21, 29 of leads 18, 20, 28, respectively, may be ring electrodes, segmented electrodes or partial ring electrodes. Segmented and partial ring electrodes each extend along an arc less than 360 degrees (e.g., 90-120 degrees) around the outer perimeter of the respective lead 18, 20, 28. In examples, one or more of leads 18, 20, 28 may be, at least in part, paddle-shaped (i.e., a "paddle" lead) and include pad electrodes positioned on a distal paddle surface.

In some examples, one or more of electrodes 19, 21, 29 may be cuff electrodes that are configured to extend at least partially around a nerve (e.g., extend axially around an outer surface of a nerve). Delivering stimulation via one or more cuff electrodes and/or segmented electrodes may help achieve a more uniform electrical field or activation field distribution relative to the nerve, which may help minimize discomfort to patient 14 that results from the delivery of stimulation therapy.

The illustrated numbers and configurations of leads 18, 20, and 28 and electrodes carried by leads 18, 20, and 28 are merely exemplary. Other configurations, i.e., number and position of leads and electrodes, are possible. For example, IMD 16 may be coupled to additional leads or lead segments having one or more electrodes positioned at different locations in the pelvic region of patient 14. The additional leads may be used for delivering stimulation therapies to respective stimulation sites within patient 14 or for monitoring one or more physiological parameters of patient 14. In an example in which the target therapy sites for the stimulation therapies are different, IMD 16 may be coupled to two or more leads, e.g., for bilateral or multi-lateral stimulation. As another example, IMD 16 may be coupled to a fewer number of leads, e.g., just lead 28.

In some examples, IMD 16 may deliver high frequency (HF) stimulation therapy based on patient input. In some examples, patient 14 may provide patient input using external programmer 24 or by tapping over IMD 16 when IMD 16 includes a motion sensor that is responsive to tapping. Using programmer 24, patient 14 may provide input to IMD 16 that indicates an urge felt by the patient, a leakage incident experienced by the patient, an imminent voiding event predicted by the patient, or a voluntary voiding event to be undertaken by the patient. In this way, therapy system 10 provides patient 14 with direct control of stimulation therapy.

In the illustrated example of FIG. 1, IMD 16 determines an impedance through bladder 12, which varies as a function of the contraction of bladder 12, via electrodes 19 and 21 on leads 18 and 20, respectively. In the example shown in FIG. 1, IMD 16 determines bladder impedance using a four-wire (or Kelvin) measurement technique. In other examples, IMD 16 may measure bladder impedance using a two-wire sensing arrangement. In either case, IMD 16 may transmit an electrical measurement signal, such as a current, through bladder 12 via leads 18 and 20, and determine bladder impedance based on the measurement of the transmitted electrical signal.

In the example four-wire arrangement shown in FIG. 1, electrodes 19A and 21A and electrodes 19B and 21B, may be located substantially opposite each other relative to the center of bladder 12. For example, electrodes 19A and 21A may be placed on opposing sides of bladder 12, either anterior and posterior or left and right. In FIG. 1, electrodes 19 and 21 are shown placed proximate to an exterior surface of the wall of bladder 12. In some examples, electrodes 18 and 21 may be sutured or otherwise affixed to the bladder wall. In other examples, electrodes 19 and 21 may be implanted within the bladder wall. To measure the impedance of bladder 12, IMD 16 may source an electrical signal, such as current, to electrode 19A via lead 18, while electrode 21A via lead 20 sinks the electrical signal. IMD 16 may then determine the voltage between electrode 19B and electrode 21B via leads 18 and 20, respectively. IMD 16 determines the impedance of bladder 12 using a known value of the electrical signal sourced and the determined voltage.

In the example of FIG. 1, IMD 16 also includes a sensor 22 for detecting changes in the contraction of bladder 12. Sensor 22 may be, for example, a pressure sensor for detecting changes in bladder pressure, electrodes for sensing pudendal or sacral afferent nerve signals, or electrodes for sensing urinary sphincter EMG signals, or any combination thereof. In examples in which sensor 22 is a pressure sensor, the pressure sensor may be a remote sensor that wirelessly transmits signals to IMD 16 or may be carried on one of leads 18, 20, or 28 or an additional lead coupled to IMD 16. In examples in which sensor 22 includes one or more electrodes for sensing afferent nerve signals, the sense electrodes may be carried on one of leads 18, 20, or 28 or an additional lead coupled to IMD 16. In examples in which sensor 22 includes one or more sense electrodes for generating a urinary sphincter EMC the sense electrodes may be carried on one of leads 18, 20, or 28 or additional leads coupled to IMD 16. In any case, in some examples, IMD 16 may control the delivery of electrical stimulation based on input received from sensor 22. For example, IMD 16 may initiate the delivery of HF stimulation to inhibit the contract of bladder 12 when the sensor 22 indicates an increase in the probability of an involuntary voiding event of patient 14, such as when an increase in bladder pressure is detected by sensor 22.

In other examples, sensor 22 may comprise a patient motion sensor that generates a signal indicative of patient activity level or posture state. In some examples, IMD 16 controls the delivery of stimulation therapy to patient 14 based on sensed patient activity level or posture state. For example, a patient activity level that is greater than or equal to a threshold may indicate that there is an increase in urgency and/or an increase in the probability that an incontinence event will occur, and accordingly, IMD 16 may provide electrical stimulation based on the patient activity level. In one example, the IMD 16 may deliver HF stimulation to inhibit bladder contractions in response to a patient activity level that is greater than the threshold, since there may be an increase in urgency and/or an increase in the probability that an incontinence event may occur. The inhibition of bladder contraction due to the delivery of HF stimulation may reduce the probability that an incontinence event may occur.

As an additional example, patient 14 may be more prone to an incontinence event when patient 14 is in an upright posture state compared to a lying down posture state. Accordingly, in some examples, IMD 16 may control the delivery of electrical stimulation to patient based on the patient posture state determined based on a signal generated by sensor 22. For example, IMD 16 may deliver HF stimulation to inhibit bladder when sensor 22 indicates that patient 14 is in a posture that is more prone to an incontinence event in order reduce the probability of an incontinence event.

As another example, sensor 22 may generate a signal indicative of patient motion and IMD 16 or programmer 24 may determine whether patient 14 voluntarily voided based on a pattern in the patient motion signal associated with a voluntary voiding event alone or in combination with other sensed parameters (e.g., bladder impedance).

System 10 includes an external programmer 24, as shown in FIG. 1. In some examples, programmer 24 may be a wearable communication device, handheld computing device, computer workstation, or networked computing device. Programmer 24 may include a user interface that receives input from a user (e.g., patient 14, a patient caretaker or a clinician). The user interface may include a keypad and a display (e.g., an LCD display). The keypad may take the form of an alphanumeric keypad or a reduced set of keys associated with particular functions of programmer 24. Programmer 24 can additionally or alternatively include a peripheral pointing device, such as a mouse, via which a user may interact with the user interface. In some examples, a display of programmer 24 may include a touch screen display, and a user may interact with programmer 24 via the touch screen display. It should be noted that the user may also interact with programmer 24 and/or IMD 16 remotely via a networked computing device.

Patient 14 may interact with programmer 24 to control IMD 16 to deliver the stimulation therapy, to manually abort the delivery of the stimulation therapy by IMD 16 while IMD 16 is delivering the therapy or is about to deliver the therapy, or to inhibit the delivery of the stimulation therapy by IMD 16, e.g., during voluntary voiding events. Patient 14 may, for example, use a keypad or touch screen of programmer 24 to cause IMD 16 to deliver the stimulation therapy, such as when patient 14 senses that a leaking episode may be imminent. In this way, patient 14 may use programmer 24 to control the delivery of the stimulation therapy "on demand," e.g., when extra stimulation therapy is desirable.

Patient 14 may interact with programmer 24 to terminate the delivery of the stimulation therapy during voluntary voiding events or to modify the type of stimulation therapy that is delivered (e.g., to control IMD 16 to deliver stimulation therapy to help patient 14 voluntarily void in examples in which patient 14 has a urinary retention disorder). That is, patient 14 may use programmer 24 to enter input that indicates the patient will be voiding voluntarily. When IMD 16 receives the input from programmer 24, IMD 16 may suspend delivery the stimulation therapy for a predetermined period of time, e.g., two minutes, to allow the patient to voluntarily void, or switch to a different type of stimulation therapy to help patient 14 voluntarily void.

A user, such as a physician, technician, surgeon, electrophysiologist, or other clinician, may also interact with programmer 24 or another separate programmer (not shown), such as a clinician programmer to communicate with IMD 16. Such a user may interact with a programmer to retrieve physiological or diagnostic information from IMD 16. The user may also interact with a programmer to program IMD 16, e.g., select values for the stimulation parameter values of the therapy cycle with which IMD 16 generates and delivers electrical stimulation and/or the other operational parameters of IMD 16. For example, the user may use programmer 24 to retrieve information from IMD 16 regarding the contraction of bladder 12 and voiding events. As another example, the user may use programmer 24 to retrieve information from IMD 16 regarding the performance or integrity of IMD 16 or other components of system 10, such as leads 18, 20, and 28, or a power source of IMD 16.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

In some examples, IMD 16 controls the delivery of HF stimulation to inhibit bladder contraction based on patient input from programmer 24 and/or sensor data (e.g., generated by sensor 22). Sensor data may include measured signals relating to urinary incontinence, e.g., bladder impedance, bladder pressure, pudendal or sacral afferent nerve signals, a urinary sphincter EMG, or any combination thereof. As another example, sensor data may include, and IMD 16 may deliver stimulation therapy in response to, measured signals relating to a patient activity level or patient posture state. In some instances, sensor data may be indicative of an increased probability of an occurrence of an involuntary voiding event.

Bladder contraction may be less likely immediately after a voiding event and/or the possibility of an involuntary voiding event may be relatively low immediately after a voiding event. Therefore, the delivery of HF stimulation to inhibit bladder contraction may not be necessary to prevent or at least minimize the possibility of an involuntary voiding event during the time period immediately following the occurrence of a voluntary or involuntary voiding event. In contrast, bladder contraction may be more likely as time passes since the last voiding event and/or the possibility of an involuntary voiding event may increase as time passes since the last voiding event. Accordingly, IMD 16 may delivery HF stimulation to inhibit bladder contraction only after a period of time has passed since the last voiding event. For example, IMD 16 may be configured to deliver HF electrical stimulation to inhibit bladder contraction only after fill level of the bladder is determined to be above a threshold level (e.g., some fill level associated with a high probability of an involuntary voiding event).

Figure 2:
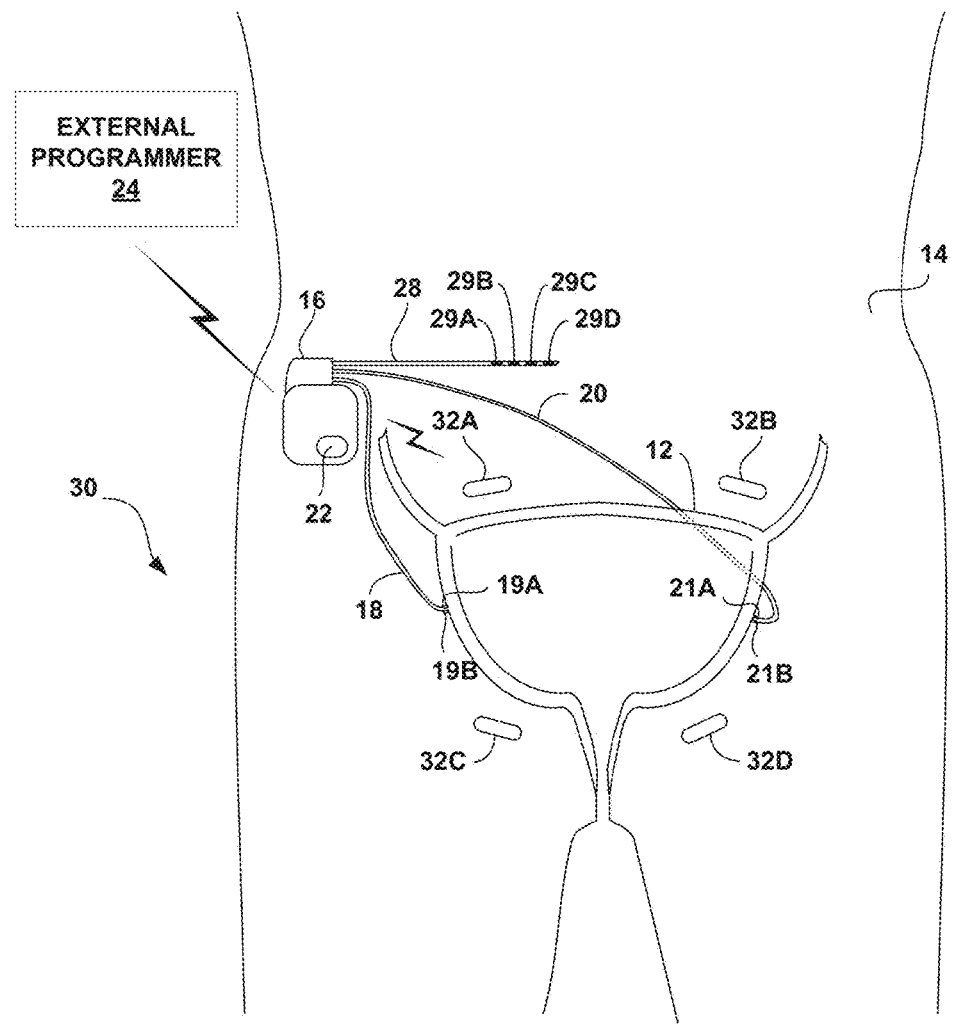
FIG. 2 is a conceptual diagram illustrating another example therapy system that delivers stimulation therapy to a patient to manage a patient condition such as, e.g., incontinence.

FIG. 2 is conceptual diagram illustrating another example therapy system 30 that delivers stimulation therapy to manage, e.g., urinary incontinence or other condition of patient 14. Therapy system 30 includes a distributed array of electrical stimulators, referred to herein as microstimulators 32A-32D (collectively referred to as "microstimulators 32"), in addition to IMD 16, leads 18, 20, and 28, sensor 22, and programmer 24. Microstimulators 32 are configured to generate and deliver electrical stimulation therapy to patient 14 via one or more electrodes. Microstimulators 32 have a smaller size than IMD 16, and are typically leadless.

IMD 16 may deliver electrical stimulation therapies to patient 14 via microstimulators 32. For example, IMD 16 may communicate wirelessly with microstimulators 32 via wireless telemetry to control delivery of the stimulation therapies via microstimulators 32. In the example of FIG. 2, microstimulators 32 are implanted at different target stimulation sites. For example, microstimulators 32A and 32B may be positioned to stimulate a different set of nerves than microstimulators 32C and 324D. As an example, microstimulators 32A and 32B may target sacral nerves, while microstimulators 32C and 32D target the pudendal nerve. In other examples, microstimulators 32 may be implanted at various locations within the pelvic floor region, e.g., at different positions in proximity to the sacrum to target different nerves within the pelvic region. The illustrated number and configuration of microstimulators 32 is merely exemplary. Other configurations, i.e., number and position of microstimulators, are possible.

Systems 10 and 30 shown in FIGS. 1 and 2, respectively, are merely examples of therapy systems that may provide a stimulation therapy to manage urgency and/or urinary incontinence. Systems with other configurations of leads, electrodes, and sensors are possible. Additionally, in other examples, a system may include more than one IMD.

Figure 3:
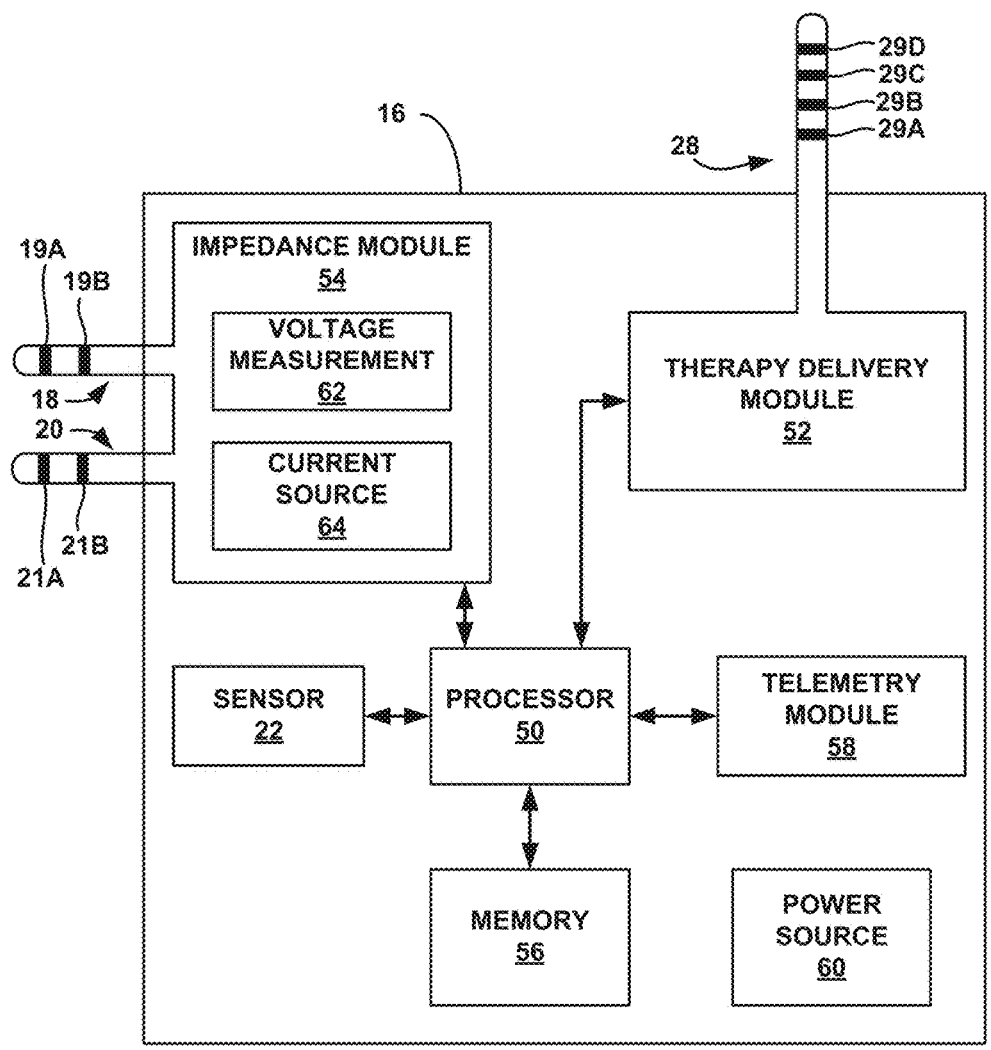
FIG. 3 is a functional block diagram illustrating an example configuration of the implantable medical device (IMD) of the systems shown in FIGS. 1 and 2.

FIG. 3 is a functional block diagram illustrating example components of IMD 16. In the example of FIG. 3, IMD 16 includes sensor 22, processor 50, therapy delivery module 52, impedance module 54, memory 56, telemetry module 58, and power source 60.

Therapy delivery module 52 generates and delivers electrical stimulation under the control of processor 50. In particular, processor 50 controls therapy delivery module 52 by accessing memory 56 to selectively access and load therapy programs into therapy delivery module 52. Therapy delivery module 52 generates and delivers electrical stimulation according to the therapy programs. In some examples, therapy delivery module 52 generates therapy in the form of electrical pulses. In other examples, therapy delivery module 52 may generate electrical stimulation in the form of continuous waveforms.

Patient 14 may provide patient input to IMD 16 using programmer 24 or another device, or directly via IMD 16. For example, patient 14 may provide patient input to IMD 16 using sensor 22 when sensor 22 includes a motion sensor that is responsive to tapping (e.g., by patient 14) on skin superior to IMD 16. When sensor 22 includes a motion sensor that is responsive to tapping, upon detecting the pattern of tapping that indicates a particular patient input, processor 50 may determine that the patient input was received.

Regardless of whether patient input is received from programmer 24 or other device, the patient input may indicate an urge felt by patient 14, a leakage incident experienced by patient 14, an imminent voiding event predicted by patient 14, a voluntary voiding event undertaken by patient 14 or other information that may affect the timing or intensity level of stimulation delivered by IMD 16.

In the example of FIG. 3, therapy delivery module 52 is electrically coupled to a single lead 28, and therapy delivery module 52 delivers electrical stimulation to a tissue site of patient 14 via selected electrodes 29A-29D carried by lead 28. A proximal end of lead 28 extends from the housing of IMD 16 and a distal end of lead 28 extends to one or more target therapy sites within the pelvic floor, such as tissue sites proximate a sacral nerve, a pudendal nerve, a hypogastric nerve, a urinary sphincter, or any combination thereof. In other examples, therapy delivery module 52 may deliver electrical stimulation with electrodes on more than one lead and each of the leads may carry one or more electrodes. The leads may be configured as axial leads with ring electrodes and/or paddle leads with electrode pads arranged in a two-dimensional array. Additionally, or alternatively, the leads may include segmented and/or partial ring electrodes. The electrodes may operate in a bipolar or multi-polar configuration with other electrodes, or may operate in a unipolar configuration referenced to an electrode carried by the device housing or "can" of IMD 16. In yet other examples, such as system 30 shown in FIG. 2 that includes microstimulators 32, processor 50 may act as a "master" module that controls microstimulators to deliver stimulation at target therapy sites. In other examples, however, one of microstimulators 32 may act as a master module or microstimulators 32 may be self-controlled.

In some examples, processor 50 controls therapy module 52 to deliver the stimulation therapy to patient 14 based on signals received from impedance module 54, sensor 22, or patient input received via telemetry module 58. In the example shown in FIG. 3, processor 50 monitors bladder impedance to detect bladder contractions based on signals received from impedance module 54. For example, processor 50 may determine an impedance value based on signals received from impedance module 54, and a particular impedance value may be associated with a bladder contraction (e.g., based on data obtained during a programming period). Therapy module 52 may deliver electrical stimulation therapy to patient 14 based on detection of bladder contraction using impedance module 54. For example, therapy module 52 may deliver HF electrical stimulation to inhibit bladder contraction in response to detection of an impedance value that indicates that the likelihood of a bladder contraction is increasing in order to address a possible increase likelihood of unintentional voiding. In other examples, therapy module 52 may deliver HF electrical stimulation to inhibit bladder contraction in response to detection of an impedance value (e.g., a low impedance value) that indicates that the bladder is filling in order to address a possible increase in the likelihood of unintentional voiding. In still other examples, a high impedance value may indicate that the bladder is empty, for example, after a voiding event.

In the example of FIG. 3, impedance module 54 includes voltage measurement circuitry 62 and current source 64, and may include an oscillator (not shown) or the like for producing an alternating signal, as is known. In some examples, as described above with respect to FIG. 1, impedance module 54 may use a four-wire, or Kelvin, arrangement. As an example, processor 50 may periodically control current source 64 to, for example, source an electrical current signal through electrode 19A and sink the electrical current signal through electrode 21A. Impedance module 54 may also include a switching module (not shown) for selectively coupling electrodes 19A, 19B, 21A, and 21B to current source 64 and voltage measurement circuitry 62. Voltage measurement circuitry 62 may measure the voltage between electrodes 19B and 21B. Voltage measurement circuitry 62 may include sample and hold circuitry or other suitable circuitry for measuring voltage amplitudes. Processor 50 determines an impedance value from the measured voltage values received from voltage measurement circuitry 52.

Processor 50 may delivery HF stimulation to inhibit bladder contraction based on signals received from sensor 22 in addition to, or instead of, impedance module 54. In examples in which sensor 22 includes a pressure sensor, processor 50 may determine a bladder pressure value based on signals received from the pressure sensor. Processor 50 may determine whether contractions of bladder 12 are indicative an imminent incontinence event, for example, based on comparison of the sensed pressure to a pressure threshold that indicates an imminent event. For example, processor 50 may detect an imminent incontinence event when the sensed pressure is greater than the pressure threshold. Accordingly, in some examples, therapy delivery module 52, under control of processor 50, may deliver HF electrical stimulation to inhibit bladder contraction when sensed pressure is greater than the pressure threshold.

In examples in which sensor 22 includes a motion sensor, processor 50 may determine a patient activity level or posture state based on a signal generated by sensor 22. For example, processor 50 may determine a patient activity level by sampling the signal from sensor 22 and determining a number of activity counts during a sample period, where a plurality of activity levels are associated with respective activity counts. In one example, processor 50 compares the signal generated by sensor 22 to one or more amplitude thresholds stored within memory 56, and identifies each threshold crossing as an activity count.

Processor 50 may determine a patient posture state based on a signal from sensor 22 using any suitable technique. In one example, a posture state may be defined as a three-dimensional space (e.g., a posture cone or toroid), and whenever a posture state parameter value, e.g., a vector from a three-axis accelerometer of sensor 22 resides within a predefined space, processor 50 indicates that patient 14 is in the posture state associated with the predefined space.

Certain posture states or activity levels may be associated with a higher incidence of incontinence events. For example, patient 14 may have less control of the pelvic floor muscles when occupying an upright posture state or when patient 14 is in a highly active state (e.g., as indicated by a stored activity count or a threshold activity signal value). Thus, detection of these activity levels or posture states may be triggers for the delivery of HF stimulation therapy. For example, therapy delivery module 52 may, under control of processor 50, deliver HF electrical stimulation when sensed activity levels or patient posture indicates an increased probability that an incontinence event may occur.

The threshold values stored in memory 56 may be determined using any suitable technique. In some examples, the threshold values may be determined during implantation of IMD 16 or during a trial period in a clinician's office following the implant procedure. For example, a clinician may record impedance values during involuntary voiding events and use the recorded impedance values or values calculated based on the recorded values as threshold values. These threshold values may be adapted over time based on patient input, e.g., via external programmer 24. As an example, patient 14 may indicate, via programmer 24, when an involuntary voiding event takes place. When the patient input is received, processor 50 may determine an impedance value during the event or immediately prior to the event based on signals received from impedance module 54. A new threshold value may be determined using this impedance value. For example, the threshold value stored may be a running average of impedance values measured during involuntary voiding events.

In some examples, IMD 16 includes impedance sensing module 54 and not sensor 22, while in other examples IMD 16 includes sensor 22 but not impedance sensing module 54. Moreover, in some examples, sensor 22 and/or impedance sensing module 54 may be physically separate from IMD 16. Physically separate sensors may be useful in examples in which either sensor 22 and/or impedance sensing module 54 sense one or more physiological parameters at a location that is not accessible by IMD 16 or difficult to access by IMD 16.

Processor 50 may control therapy delivery module 52 to deliver stimulation therapy based on patient input received via telemetry module 58. Telemetry module 58 includes any suitable hardware, firmware, software or any combination thereof for communicating with another device, such as programmer 24 (FIG. 1). Under the control of processor 50, telemetry module 58 may receive downlink telemetry, e.g., patient input, from and send uplink telemetry to programmer 24 with the aid of an antenna, which may be internal and/or external. Processor 50 may provide the data to be uplinked to programmer 24 and the control signals for the telemetry circuit within telemetry module 58, and receive data from telemetry module 58.

Processor 50 may control telemetry module 58 to exchange information with medical device programmer 24. Processor 50 may transmit operational information and receive stimulation programs or stimulation parameter adjustments via telemetry module 58. Also, in some examples, IMD 16 may communicate with other implanted devices, such as stimulators, control devices, or sensors, via telemetry module 58.

The processors described in this disclosure, such as processor 50 and processing circuitry in impedance module 54 and other modules, may be one or more digital signal processors (DSPs), general purpose microprocessors, application specific integrated circuits (ASICs), field programmable logic arrays (FPGAs), or other equivalent integrated or discrete logic circuitry, or combinations thereof. The functions attributed to processors described herein may be provided by a hardware device and embodied as software, firmware, hardware, or any combination thereof. In some examples, the processing circuitry of impedance module 54 that determines an impedance based on a measured voltage and/or current of a signal may be the same microprocessor, ASIC, DSP, or other digital logic circuitry that forms at least part of processor 50.

Memory 56 stores instructions for execution by processor 50, in addition to therapy cycles. In some examples, memory 56 store patient parameter information, such as information generated by impedance module 54 and/or sensor 22. For example, information related to measured impedance and determined posture may be recorded for long-term storage and retrieval by a user, or used by processor 50 for adjustment of stimulation parameters, such as amplitude, pulse width, and pulse rate. Memory 56 may include separate memories for storing instructions, electrical signal information, programs, and other data.

In addition to the stimulation frequencies described herein, example ranges of electrical stimulation parameters that may be used in the electrical stimulation therapy are listed below. While stimulation pulses are described, stimulation signals may be of any of a variety of forms such as sine waves or the like.

Amplitude: between approximately 0.1 volts and 50 volts, such as between approximately 0.5 volts and 20 volts, or between approximately 0.1 volt and 10 volts. In other embodiments, a current amplitude may be defined as the biological load in the voltage that is delivered. For example, the range of current amplitude may be between approximately 0.1 milliamps (mA) and 50 mA.

Pulse Width: between about 10 microseconds and 5000 microseconds. In some examples, the pulse width may be between approximately 40 microseconds and 1000 microseconds or between approximately 100 microseconds and 300 microseconds.

In some examples, the stimulation parameters may define a therapy with an intensity below a motor and/or perception threshold of the target tissue being stimulation. For example, the stimulation may have an intensity below a motor threshold such that the stimulation does not result in a motor evoked potential in the stimulation tissue. As another example, the stimulation may have an intensity below a perception threshold such that the stimulation is not perceived by patient 14.

Memory 56 may include any volatile, non-volatile, magnetic, or electrical media, such as a random access memory (RAM), read-only memory (ROM), non-volatile RAM (NVRAM), electrically-erasable programmable ROM (EEPROM), flash memory, and the like. Memory 56 may store program instructions that, when executed by processor 50, cause IMD 16 to perform the functions ascribed to IMD 16 herein.

Power source 60 delivers operating power to the components of IMD 16. Power source 60 may include a battery and a power generation circuit to produce the operating power. In some examples, the battery may be rechargeable to allow extended operation. Recharging may be accomplished through proximal inductive interaction between an external charger and an inductive charging coil within IMD 16. In other examples, an external inductive power supply may transcutaneously power IMD 16 whenever stimulation therapy is to occur.

Figure 4:
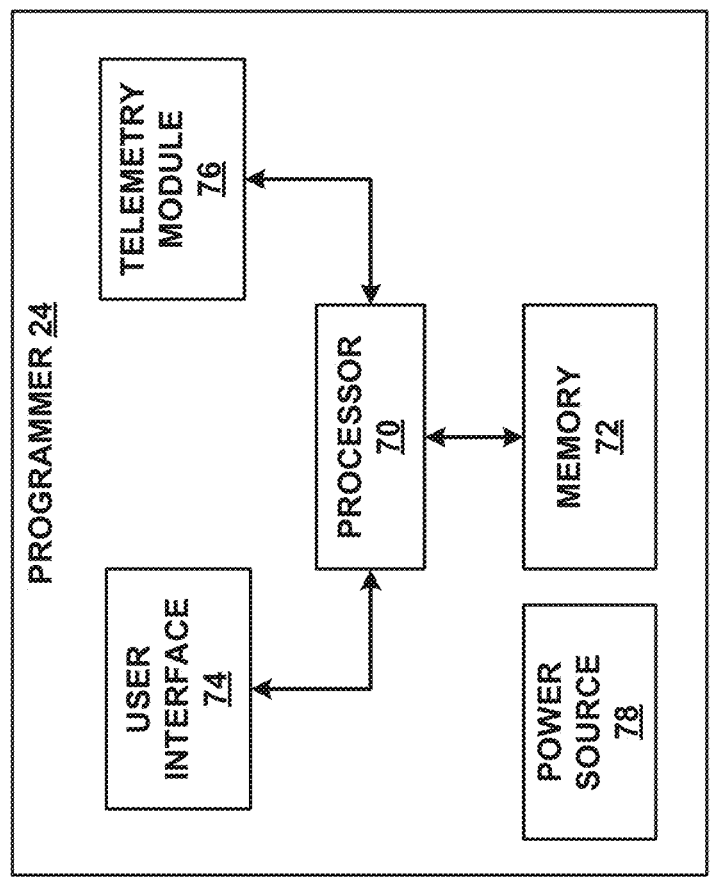
FIG. 4 is a functional block diagram illustrating an example configuration of the external programmer of the systems shown in FIGS. 1 and 2.

FIG. 4 is a functional block diagram illustrating example components of external programmer 24. While programmer 24 may generally be described as a hand-held computing device, the programmer may be a notebook computer, a cell phone, or a workstation, for example. As illustrated in FIG. 4, external programmer 24 may include a processor 70, memory 72, user interface 74, telemetry module 76, and power source 78. Memory 72 may store program instructions that, when executed by processor 70, cause processor 70 to provide the functionality ascribed to programmer 24 throughout this disclosure.

In some examples, memory 72 may further include therapy cycles defining stimulation therapy, similar to those stored in memory 56 of IMD 16. The therapy cycles stored in memory 72 may be downloaded into memory 56 of IMD 16. Memory 72 may include any volatile, non-volatile, fixed, removable, magnetic, optical, or electrical media, such as RAM, ROM, CD-ROM, hard disk, removable magnetic disk, memory cards or sticks, NVRAM, EEPROM, flash memory, and the like. Processor 70 can take the form one or more microprocessors, DSPs, ASICs, FPGAs, programmable logic circuitry, or the like, and the functions attributed to processor 70 herein may be embodied as hardware, firmware, software or any combination thereof.

User interface 74 may include a button or keypad, lights, a speaker for voice commands, and a display, such as a liquid crystal (LCD). In some examples the display may be a touch screen. As discussed in this disclosure, processor 70 may present and receive information relating to stimulation therapy via user interface 74. For example, processor 70 may receive patient input via user interface 74. The patient input may be entered, for example, by pressing a button on a keypad or selecting an icon from a touch screen. Patient input may include, but is not limited to, input that indicates an urge felt by the patient, a leakage incident experienced by the patient, an imminent voiding event predicted by the patient, or a voluntary voiding event to be undertaken by the patient.

Telemetry module 76 supports wireless communication between IMD 16 and external programmer 24 under the control of processor 70. Telemetry module 76 may also be configured to communicate with another computing device via wireless communication techniques, or direct communication through a wired connection. Telemetry module 76 may be substantially similar to telemetry module 58 described above, providing wireless communication via an RF or proximal inductive medium. In some examples, telemetry module 76 may include an antenna, which may take on a variety of forms, such as an internal or external antenna. An external antenna that is coupled to programmer 24 may correspond to a programming head that may be placed over IMD 16.

Examples of local wireless communication techniques that may be employed to facilitate communication between programmer 24 and another computing device include RF communication according to IEEE 802.11 or Bluetooth specification sets, infrared communication, e.g., according to an IrDA standard, or other standard or proprietary telemetry protocols. In this manner, other external devices may be capable of communicating with programmer 24 without needing to establish a secure wireless connection.

In some cases, it may be desirable for IMD 16 to decrease the frequency of stimulation or even suspend the delivery of the HF stimulation configured to inhibit bladder contractions of patient 14 when patient 14 needs to void. In some examples, patient 14 may interact with programmer 24 (or directly with IMD 16 as described above) to control IMD 16 to withhold the stimulation that is intended to inhibit bladder contractions. Patient 14 may indicate an intent to void via user interface 74, and processor 70 may implement a blanking interval through communication of the indication to IMD 16 via telemetry module 76. For example, processor 70 may transmit a command signal to IMD 16 that indicates IMD 16 should temporarily suspend delivery of the stimulation therapy in response to command signal. In some cases, this may permit voluntary voiding by patient 14.

In other examples, IMD 16 may automatically determine when patient 14 is attempting to voluntary void, e.g., based on a voiding signature of an EMG signal indicative of bladder activity or based on bladder pressure or contraction. In such examples, IMD 16 may automatically suspend the delivery of electrical stimulation therapies to permit patient 14 to voluntary void. In some cases, suspension of stimulation by IMD 16 is not necessary to facilitate voiding, and stimulation may occur substantially simultaneously with the voluntary voiding. For example, the bladder volume will eventually increase to a level to trigger strong bladder contractions that prevails over the stimulation therapy to allow voiding.

Power source 78 delivers operating power to the components of programmer 24. Power source 78 may include a battery, for example a rechargeable battery. Recharging may be accomplished by using an alternating current (AC) outlet or through proximal inductive interaction between an external charger and an inductive charging coil within programmer 24.

Figure 5:
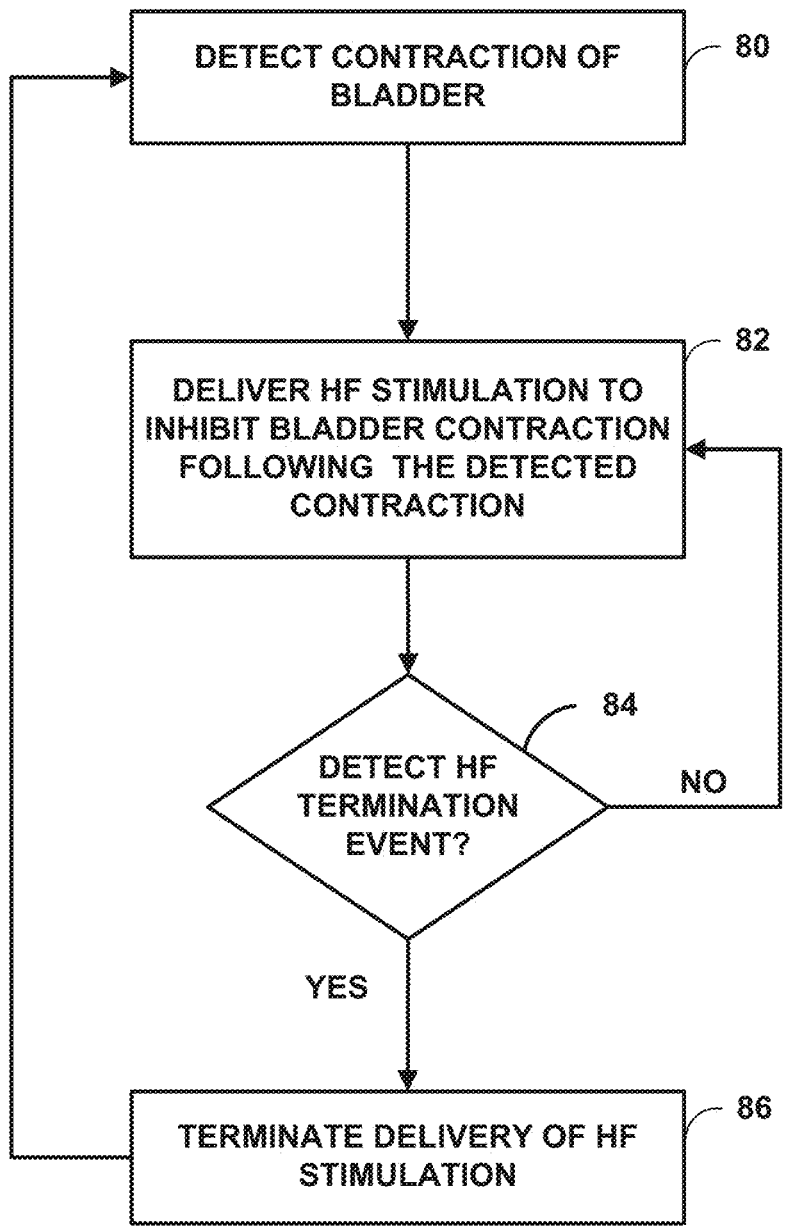
FIG. 5 is a flow diagram illustrating an example technique for delivering stimulation therapy to a patient to manage urinary incontinence.

FIG. 5 is a flow diagram of an example technique for delivering electrical stimulation to patient 14 to inhibit bladder contraction using HF stimulation. In some examples, the technique of FIG. 5 may be implemented as a set of instructions executable by processor 50 and stored by memory 56 of IMD 16 or a memory of another device. While processor 50 and memory 56 are primarily referred to throughout the description of FIG. 5, in other examples, a processor of another device (e.g., programmer 24) may perform any part of the techniques described herein, including the technique shown in FIG. 5, alone or in combination with another device. Although FIG. 5 is described with regard to system 10 of FIG. 1, other systems and devices employing the technique of FIG. 5 are contemplated.

According to the example method of FIG. 5, processor 50 of IMD 16 detects a bladder contraction using any suitable technique (80). For example, processor 50 may detect the bladder contraction based on sensor data received from sensor 22 that indicates measured signals relating to bladder impedance, bladder pressure, and/or muscle activity associated with a bladder contraction, e.g., such as a contraction associated with a voiding event. For example, a bladder impedance value may decrease as the volume of urine within bladder 12 increases. Accordingly, processor 50 may detect that bladder 12 has emptied based on an increase (e.g., a threshold amount of increase) in bladder impedance, indicating a voiding event resulting from a bladder contraction. As another example, processor 50 may detect that bladder 12 has emptied based on signals generated by sensor 22 that indicate a change from a bladder pressure (e.g., a threshold amount of pressure change) that indicates a relatively full bladder to a bladder pressure that indicates a relatively empty bladder. Other techniques of detecting a bladder contraction using a sensor may also be used. For example, in some implementations, one or more sensors that may communicate with IMD 16 or programmer 24 may be incorporated into an undergarment of patient 14 that detect wetting, fluid pH, or other characteristics that identifies fluid as urine, indicating a voiding event resulting from a bladder contraction. The sensors incorporated into the undergarment may signal processor 50 via telemetry module 58 when a bladder contraction occurs.

Processor 50 may also detect a bladder contraction (80) based on patient input received from patient programmer 24. For example, patient input may include an entry of a voiding event (indicating a bladder contraction) in patient programmer 24 using user interface 74. Additionally or alternatively, patient input may include an occurrence of urge incontinence experienced by patient 14 and/or other condition indicative of the occurrence of a bladder contraction via patient programmer 24.

Following the detected bladder contraction, processor 50 may control therapy delivery module 52 (FIG. 3) to generate and deliver electrical stimulation at HF (e.g., approximately 500 Hz or greater, such as, e.g., approximately 1 kHz or greater, or approximately 1 kHz to 100 kHz) to patient 14 (82). The electrical stimulation may be delivered to a tissue site proximate a pelvic floor nerve of patient 14 or another suitable tissue site for controlling bladder activity of patient 14. In some examples, IMD 16 delivers the HF electrical stimulation (82) immediately after the detected bladder contraction, while in other examples IMD 16 may wait a predetermined period of time (e.g., 20 minutes) after the voiding event. In the case of a bladder contraction resulting in a voiding event, delaying the delivery of the HF stimulation after detecting a bladder contraction may, for example, correspond to a window of time in which delivery of HF stimulation to inhibit bladder contractions of patient 14 is not necessary to manage a patient condition, such as, e.g., incontinence, due to the close temporal proximity to the detected bladder contraction resulting in a voiding event.

In some examples, processor 50 may control the time line with which therapy delivery module 52 delivers the HF stimulation substantially immediately or after some time delay following the bladder contraction based on sensor data and/or patient input. The sensor data and/or patient input may indicate that the inhibition of bladder contraction of patient 14 may be beneficial to manage a patient condition, such as, e.g., incontinence. For example, processor 50 may control therapy delivery module 52 to begin delivering the HF stimulation when the sensor data and/or patient input indicates one of an increased urge felt by patient 14, a leakage incident experienced by patient 14, or an imminent voiding event predicted by patient 14. Patient 14 may indicate one of the increased urge, the leakage incident experienced, or the imminent voiding event using programmer 24, and accordingly processor 50 may detect one of the above conditions based on patient input received from patient programmer 24. For example, processor 50 may detect that bladder 12 is relatively full based on a bladder impedance value, and processor 50 may therefore indirectly detect an increased urge felt by patient 14 based on the bladder impedance value. As another example, processor 50 may detect that bladder 12 is relatively full based on signals from a bladder pressure sensor, and processor 50 may, therefore, indirectly detect an increased urge felt by patient 14 based on bladder pressure. In some implementations, one or more sensors that may communicate with IMD 16 or programmer 24 may be incorporated into an undergarment of patient 14 that detects wetting, fluid pH, or other characteristics that identifies fluid as urine. The sensors incorporated into the undergarment may signal processor 50 via telemetry module 58 when a leakage incident is experienced by patient 14. Accordingly, processor 50 may detect a leakage incident experienced by patient 14 based on data received from the sensors incorporated into the undergarment.

In the above examples, processor 50 may initiate the delivery of HF electrical stimulation to patient 14 to inhibit bladder contractions (82), e.g., by blocking substantially all bladder contractions in patient 14 or preventing physiologically significant bladder contractions, following a detected bladder contraction (80). Processor 50 may continue to deliver the HF stimulation to patient 14 to inhibit bladder contraction (NO branch of 84)) until, e.g., processor 50 detects a HF stimulation termination event (84). When a HF stimulation termination event is detected (84) (YES branch of 84), processor 50 may terminate the delivery of the HF stimulation (86) and continue monitoring for the next bladder contraction of patient 14 (80). The HF termination event may be detected at a time when it is no longer desirable to inhibit the bladder contraction of patient 14 via delivery of HF stimulation. For example, the detection of the HF termination event may correspond to a point in time that uninhibited bladder contractions are desired including, e.g., at a point where it is desirable for patient 14 to voluntarily void his/her bladder.

In some examples, the HF termination event may be defined by the expiration of a timer that was started, e.g., when processor 50 initiated the delivery of HF stimulation to patient 14 (82). The length of the time may be on the order of seconds, minutes, or hours. In some examples, the length of time defined by the timer may generally correspond to a time period over which bladder 12 may become relatively full and experiencing a voiding event to empty or reduce the volume of bladder 12 may be desirable. Such a time period may be defined, e.g., based on prior micturition cycles of patient 14 or other patients. As another example, an HF stimulation termination event may be detected by processor 50 (84) based on sensed data indicating that bladder 12 has reached a threshold fill level. The threshold fill level may correspond to a fill level at which it may be desirable to empty or reduce the volume of bladder 12 via a voiding event. As described herein, the fill level of may be detected by way of a sensed parameter including, e.g., bladder impedance and bladder pressure.

In some examples, processor 50 may detect a HF termination event (84) in the form of patient input received, e.g., via programmer 24. For example, patient 14 may input a desire to voluntarily void bladder 12 via user interface 74 of programmer 24. Processor 70 may then generate and transmit an indication to IMD 16 via telemetry module 76 indicating that the HF should be terminated. Processor 50 may terminate the delivery of HF stimulation to patient 14 in response (86).

When the delivery of HF stimulation to patient 14 is terminated, bladder contractions may not longer be inhibited as when the HF stimulation was delivered to patient 14. The resulting uninhibited bladder contractions may allow patient 14 to void bladder 12. In some examples, patient 14 may experience a return to the uninhibited level of bladder contraction substantially immediately after the HF stimulation is terminated (86). Alternatively, there may be some period of time following termination of the HF stimulation during which the bladder contraction of patient 14 is inhibited to at least some degree compared to that of the bladder contraction experienced by patient 14 prior to delivery of HF stimulation. In such cases, processor 50 may be configured to take this additional period of time into account when determining when to terminate the delivery of HF stimulation to patient 14.

Figure 6:
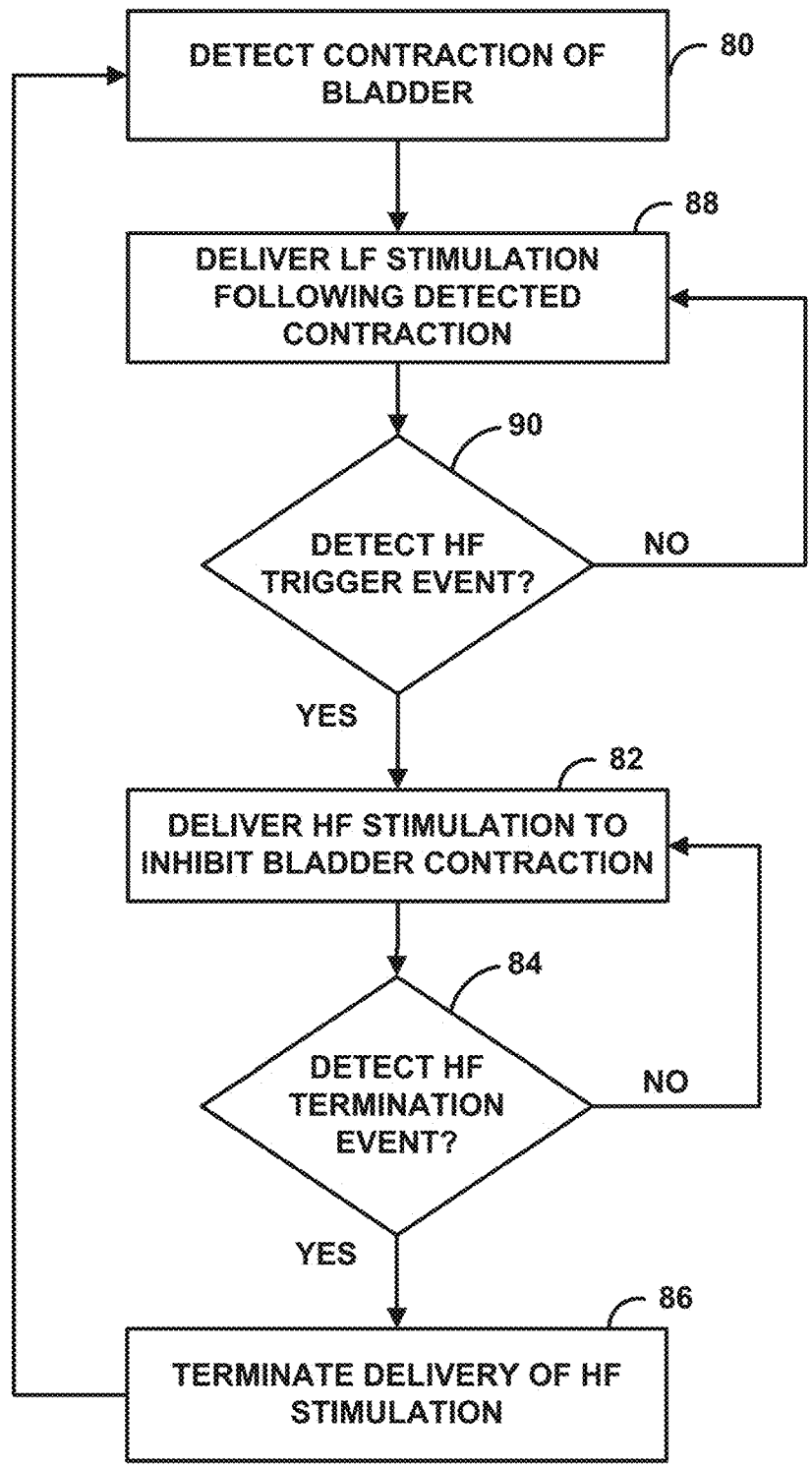
FIG. 6 is a flow diagram illustrating another example technique for delivering stimulation therapy to a patient to manage urinary incontinence.

FIG. 6 is a flow diagram illustrating another example technique for delivering HF stimulation to patient 14 to inhibit bladder contractions. In particular, the example of FIG. 6 may include the delivery of lower frequency stimulation to patient 14 in combination with the delivery of HF stimulation. Similar to that of the technique of FIG. 5, in some examples, the technique of FIG. 6 may be implemented as a set of instructions executable by processor 50 and stored by memory 56 of IMD 16 or a memory of another device. While processor 50 and memory 56 are primarily referred to throughout the description of FIG. 5, in other examples, a processor of another device (e.g., programmer 24) may perform any part of the techniques described herein, including the technique shown in FIG. 6, alone or in combination with another device.

As shown in FIG. 6, processor 50 may detect a bladder contraction of patient 14 (80), e.g., using one more of the examples described with regard to FIG. 5. Following the detected bladder contraction, processor 50 may initiate the delivery of lower frequency stimulation or "LF" stimulation to patient 14 (88). The LF stimulation may have a frequency of less than the HF stimulation, such as, e.g., a frequency of approximately 1 Hz to approximately 50 Hz, such as, e.g., between approximately 5 Hz to approximately 20 Hz, between approximately 5 Hz to approximately 15 Hz, or between approximately 10 Hz and approximately 40 Hz. The LF stimulation may treat the same patient condition (e.g., incontinence) as that treated by the HF stimulation albeit via a different physiological mechanism. Processor 50 may initiate the delivery of the LF stimulation (88) substantially immediately following the detected bladder contraction (80) or some period of time following the detected voiding event (80), e.g., after some preprogrammed period of time. The LF frequency stimulation may be delivered to the same and/or different tissue site of that of the HF stimulation.

While delivering the LF stimulation, processor 50 may detect the occurrence of a HF triggering event (90), and deliver HF stimulation based on the detection (82). Examples of HF triggering events may include those examples described with regard to FIG. 5 for initiating the delivery of HF stimulation including, e.g., sensed data, patient input, or some predetermined time period follow the detected voiding event. Processor 50 may continue delivery of the LF stimulation while also delivering the HF stimulation (82), e.g., for examples in which the LF is delivered to a target site different from that of the HF stimulation. Alternatively, the LF stimulation may not be delivered while the HF is being delivered. In some examples, for a stimulating a bilateral nerve, the LF may be delivered to one side of the nerve and the HF may be delivered to the other side of the nerve.

As shown in FIG. 6, processor 50 may deliver HF stimulation to patient 14 to inhibit bladder contraction, e.g., on a substantially continuous or periodic basis, until processor 50 detects a HF termination event 84). Once processor 50 detects a HF termination event, processor 50 may terminate or suspend the delivery of the HF stimulation patient 14 (86), e.g., as described with regard to the technique of FIG. 5.

The technique of FIG. 6 is one example of delivering LF stimulation in combination with HF stimulation following a bladder contraction but before the subsequent bladder contraction. The LF stimulation may be delivered on a substantially continuous or periodic basis. All or a portion of the LF may overlap in time with the delivery of HF stimulation to patient 16. Conversely, the LF stimulation may be interleaved with the HF stimulation such that the respective stimulation regimes alternate with each other but do not overlap in time. In some examples, processor 50 may control the delivery of stimulation such that the switch between LF stimulation and HF stimulation is substantially immediate or such that there is some time delay between the LF stimulation and HF stimulation.

EXPERIMENTAL RESULTS

A series of tests were carried out to evaluate one more aspects of examples of the disclosure. For example, tests were carried out to evaluate the influence that the delivery of HF stimulation has with regard to bladder contraction.

Experimental Procedure

Figure 8:
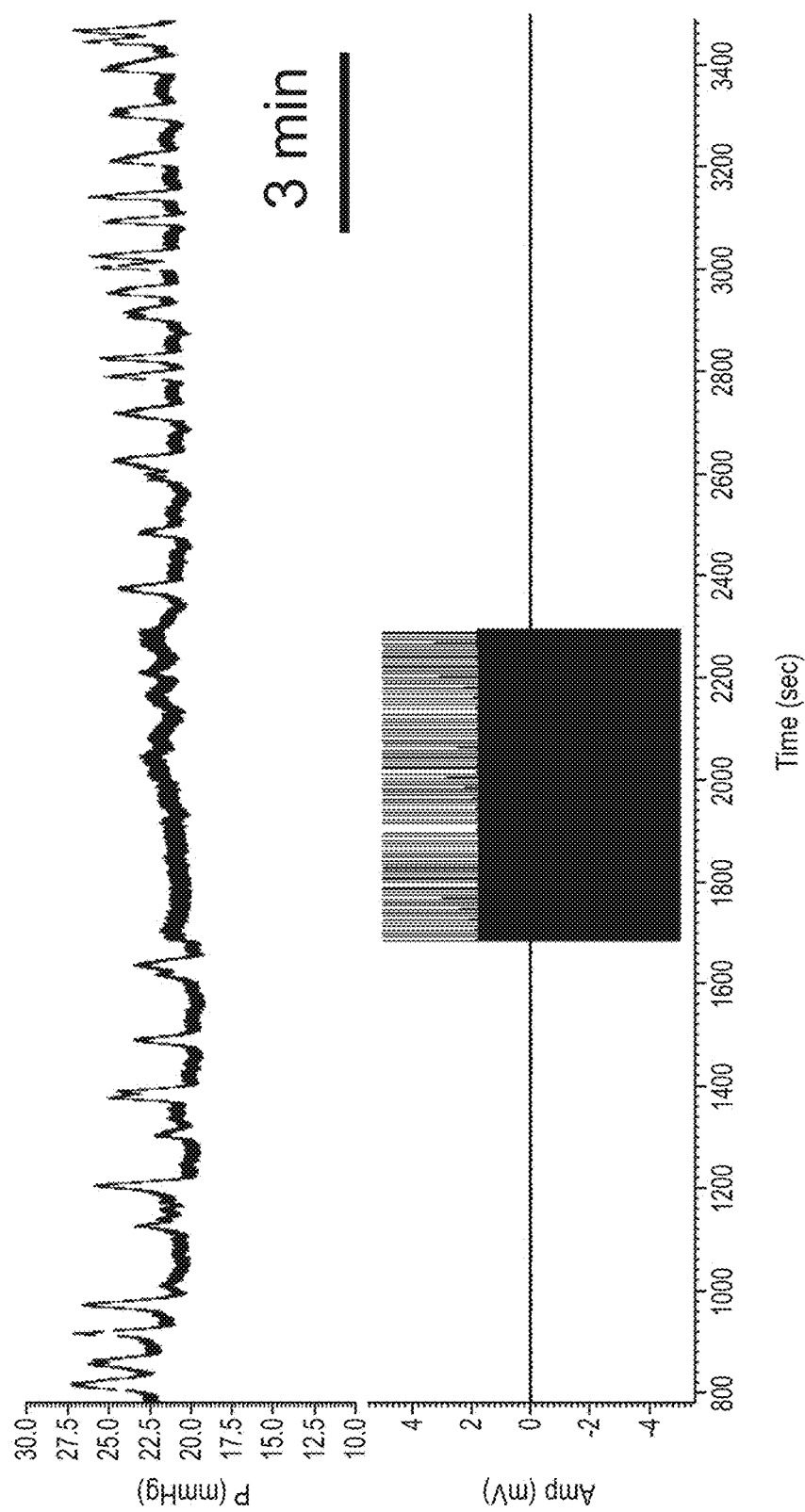
Figure 9:
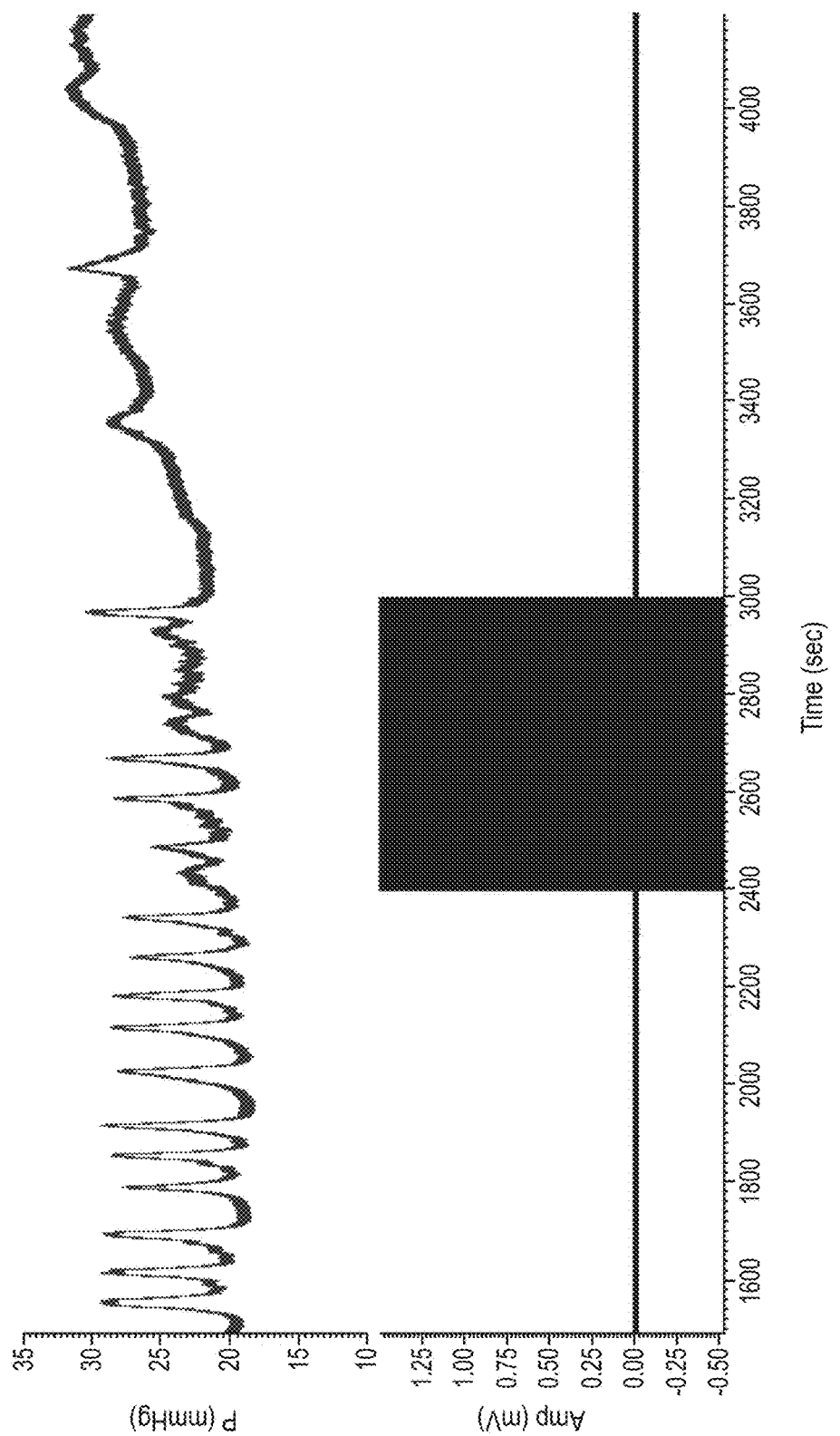

The data illustrated in FIGS. 8 and 9 were obtained from a plurality of tests performed on anesthetized female laboratory rats weighing approximately 200 grams to about 300 grams. During the tests, the body temperatures of the subjects were maintained at approximately 37° C. and bladder contractions of one or more test subjects were observed during an approximately 40-45 minute period. During the stimulation period, electrical stimulation was delivered to an L6 spinal nerve of each subject for about ten minutes, which is indicated by stimulation period in FIGS. An exposed portion of wire electrode (a Teflon-coated, 40-gauge, stainless steel wire available from Cooner Wire, Inc. of Chatsworth, Calif.) was placed under the L6 spinal nerve unilaterally or bilaterally. The electrode was connected to a S88 pulse stimulator (available from Grass Technologies of West Warwick, R.I.) through a stimulation isolation unit, which generated biphasic stimulation pulses having pulse widths of about 0.1 milliseconds and a frequency of about 10 Hz. A needle electrode served as the ground.

A cannula was placed into the bladder of each subject via the urethra and the urethra was ligated to ensure an isovolumetric bladder. To induce bladder rhythmic contractions in the subject, saline was infused into the bladder of the subject via the cannula at a rate of about 50 microliters (μL) per minute to induce a micturition reflex, which was defined in these experiments to be a bladder contraction of a magnitude greater than about 10 millimeters of mercury (mmHg). Thereafter, the infusion rate was reduced to about 10 μL a minute and continued until about three to about five consecutive contractions were established. After that time, the bladder rhythmic contractions continued until the saline infusion was terminated. The control period for determining the bladder contraction frequency control value was about 15 minutes. The bladder contractions were recorded using a pressure transducer connected to the cannula placed in the bladder of the subject. The pressure transducer output was input into a Cambridge Electronic Design (CED) data acquisition system (Cambridge, England), which is commercially available.

For each test run (i.e., each approximately 40 minute observation), a frequency of bladder contractions was determined at approximately 5 minute intervals. The determined frequencies of bladder contractions were then normalized (i.e., divided by) by a frequency of bladder contractions of the test subject prior to stimulation.

For each of the subjects in the experiments conducted to generate the data shown in FIGS. 8 and 9, the threshold intensity level was determined by determining the lowest current level at which the first visually discernible muscle contraction was evoked. The intensity of stimulation delivered to the test subject was at $T_{mot}$. In two instances, motor threshold for 10 Hz and 1 kHz was directly compared and were within 0.05 mA across the two frequencies.

Experimental Results

Based on the observations, high frequency stimulation was determined to significantly inhibit ongoing rhythmic bladder contractions (RBCs) ($p<0.05$, FIG. 7), with five of seven rats showing significant reduction in contraction frequency during stimulation.

Figure 7:
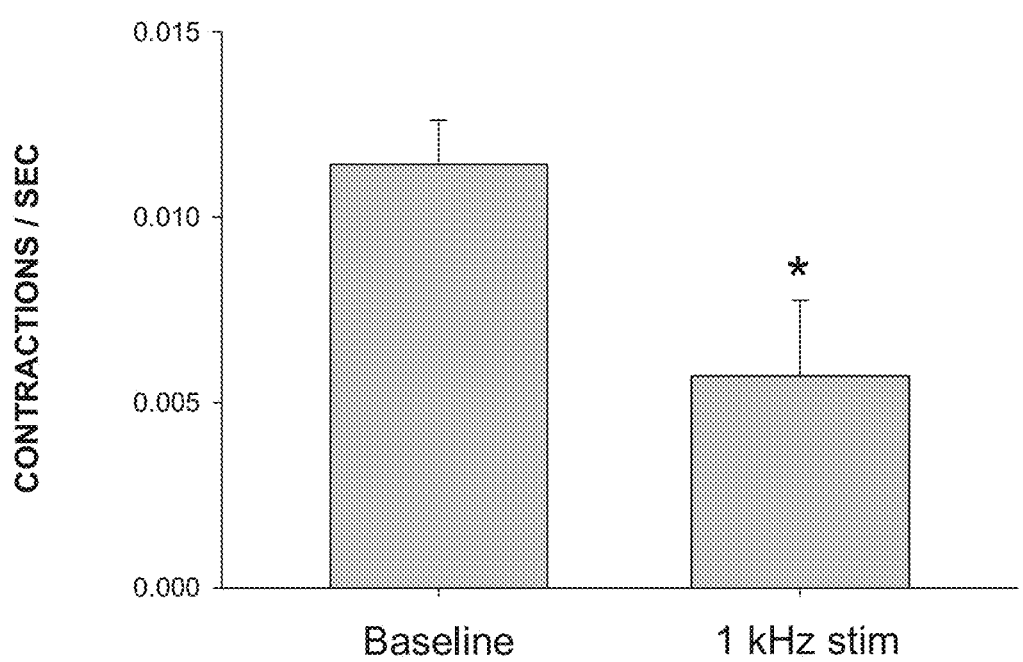
FIGS. 7-9 are plots illustrating results of experiments carried out to evaluate one or more aspects of the disclosure.

FIG. 7 is a bar chart illustrating the number of bladder contractions per second observed for a baseline specimen versus a specimen in which electrical stimulation with a frequency of approximately 1 kHz was delivered during the observation period. The baseline value was a measure of the contractions/sec for the 15 minute period prior to stimulation and 1 kHz stimulation value was the contractions/sec for the 10 minute stimulation period. The delivered stimulation was about 1 kHz, 210 μs and $T_{mot}$ for 10 minutes. For the calculated results, $p<0.05$ with Student paired t-test; n=7. As shown in FIG. 7, the number of contractions per second was reduced by over 50% in the specimen receiving the HF stimulation versus the baseline specimen.

FIG. 8 is a plot of bladder pressure (upper plot) relative the delivery of electrical stimulation (lower plot) on a temporal basis (horizontal axis). The results shown in FIG. 8 were based on measurements of two of the seven rates which displayed acute inhibition of contractions. The delivered stimulation was 1 kHz, 210 μs and $T_{mot}$ for 10 minutes. As shown, prior to and following the delivery of the HF electrical stimulation, the pressure variability indicated a relatively high frequency of bladder contraction. However, during the delivery of the HF frequency stimulation, the observed pressure was relatively constant, indicating that the bladder contraction in the specimen was inhibited by the delivery of the HF stimulation.

FIG. 9 is a plot of bladder pressure (upper plot) relative the delivery of electrical stimulation (lower plot) on a temporal basis (horizontal axis). The results shown in FIG. 9 were based on measurements of three of the seven rates which displayed acute inhibition of contractions plus some prolonged inhibition following the termination of stimulation. The delivered stimulation was 1 kHz, 210 μs and $T_{mot}$ for 10 minutes. As shown, prior to the delivery of the HF electrical stimulation, the pressure variability indicated a relatively high frequency of bladder contraction. However, during the delivery of the HF frequency stimulation, the observed pressure indicates that the bladder contractions in the specimen where inhibited by the delivery of the HF stimulation. Furthermore, the pressure observed following the termination of the HF stimulation indicates that bladder contractions were inhibited to at least some degree for a time period following the delivery of the HF stimulation.

FIGS. 8 and 9 illustrate the diversity of response patterns to 1 kHz stimulation. FIG. 8 shows a trace which results in inhibition during stimulation. FIG. 9 is an example of prolonged inhibition even after termination of the stimulus. For the group of seven rats, the bladder contractions were significantly inhibited during the ten minute stimulation period compared to the baseline contraction frequency ($p=0.033$). As a general observation, the amplitudes of contractions were not altered, though in individual cases the occasional contraction during or after stimulation showed reduced amplitude (see FIG. 9 for example).

The results indicated that high-frequency (e.g., in the kHz range) stimulation can be an effective parameter range to inhibit bladder contractions. Although not wishing to be bound by theory, the existence of a second frequency range of inhibition of RBC at high frequencies after a range of ineffective parameters (>50-100 Hz) may suggest separate mechanisms of action for stimulation at low Hz (5-30 Hz) and high (kHz) frequencies. There is a possibility that high frequency stimulation may not be 'sensed' by neurons or perceived by patients, and high frequency stimulation may be well suited for investigating other sensory modulation such as pelvic pain (interstitial cystitis, myofascial pelvic pain, etc.).

The techniques described in this disclosure may be implemented in hardware, software, firmware, or any combination thereof. In particular, the techniques may be implemented in a hardware device, such as a wireless communication device or network device, either of which may include software and/or firmware to support the implementation. For portions implemented in software, the techniques may be realized in part by a computer-readable medium comprising program code containing instructions that, when executed, performs one or more of the methods described above. In this case, the computer readable medium may comprise RAM (e.g., synchronous dynamic random access memory (SDRAM)), ROM, NVRAM, EEPROM, FLASH memory, magnetic or optical data storage media, and the like.

The program code may be executed by one or more processors, such as one or more DSPs, general purpose microprocessors, ASICs, FPGAs, or other equivalent integrated or discrete logic circuitry. In this sense, the techniques are implemented in hardware, whether implemented entirely in hardware or in hardware such as a processor executing computer-readable code. Accordingly, the term "processor," as used herein may refer to any of the foregoing structure or any other structure suitable for implementation of the techniques described herein.

The invention claimed is:

1. A method comprising:
   generating electrical stimulation therapy with a frequency of approximately 500 hertz or greater; and
   initiating delivery of the electrical stimulation therapy with the frequency of approximately 500 hertz or greater to a patient via a medical device following at least one of a contraction of a bladder or a contraction of a bowel of a patient, wherein the electrical stimulation therapy is configured to at least one of inhibit contraction of the bladder following the contraction of the bladder or inhibit contraction of the bowel following contraction of the bowel, and wherein at least one of the generating and initiating the delivery is performed via one or more processors.

2. The method of claim 1, wherein generating electrical stimulation therapy with the frequency of approximately 500 hertz or greater comprises generating electrical stimulation therapy with a frequency of 500 hertz or greater, and wherein initiating delivery of the electrical stimulation therapy with the frequency of approximately 500 hertz or greater to the patient comprises initiating delivery of the electrical stimulation therapy with the frequency of 500 hertz or greater to the patient.

3. The method of claim 1, wherein generating electrical stimulation therapy with the frequency of approximately 500 hertz or greater comprises generating electrical stimulation therapy with a frequency of 1000 hertz or greater, and wherein initiating delivery of the electrical stimulation therapy with the frequency of approximately 500 hertz or greater to the patient comprises initiating delivery of the electrical stimulation therapy with the frequency of 1000 hertz or greater to the patient.

4. The method of claim 1, wherein generating electrical stimulation therapy with the frequency of approximately 500 hertz or greater comprises generating electrical stimulation therapy with a frequency of 500 hertz to 1000 hertz, and wherein initiating delivery of the electrical stimulation therapy with the frequency of approximately 500 hertz or greater to the patient comprises initiating delivery of the electrical stimulation therapy with the frequency of 500 hertz to 1000 hertz to the patient.

5. The method of claim 1, further comprising detecting a voiding event of the patient, wherein initiating the delivery of the electrical stimulation therapy with the frequency of approximately 500 hertz or greater to the patient via the medical device comprises initiating, in response to detecting the voiding event of the patient, the delivery of the electrical stimulation therapy with the frequency of approximately 500 hertz or greater to the patient via the medical device.

6. The method of claim 1, further comprising sensing at least one of a physiological marker of the patient or patient input, wherein initiating the delivery of the electrical stimulation therapy with the frequency of approximately 500 hertz or greater to the patient via the medical device comprises initiating, in response to the sensing of the physiological marker, the delivery of the electrical stimulation therapy with the frequency of approximately 500 hertz or greater to the patient to the patient via the medical device.

7. The method of claim 6, wherein the physiological marker comprises at least one of bladder impedance, bladder pressure, bowel impedance, bowel pressure, pudendal afferent nerve activity, sacral afferent nerve activity, muscle activity, or motion of the patient.

8. The method of claim 1 wherein the electrical stimulation comprises a first electrical stimulation exhibiting a first frequency of approximately 500 hertz or greater, the method further comprising controlling delivery of a second electrical stimulation therapy to the patient via the medical device in combination with the first electrical stimulation therapy, wherein the second electrical stimulation therapy exhibits a second frequency less than the first frequency.

9. The method of claim 1, further comprising detecting the at least one of the contraction of the bladder or the contraction of the bowel of the patient, wherein initiating the delivery of the electrical stimulation therapy with the frequency of approximately 500 hertz or greater to the patient via the medical device following the at least one of the contraction of the bladder or the contraction of the bowel of a patient comprises initiating, in response to the detection of the at least one of the contraction of the bladder or the contraction of the bowel of the patient, the delivery of the electrical stimulation therapy with the frequency of approximately 500 hertz or greater to the patient via the medical device following the at least one of the contraction of the bladder or the contraction of the bowel of a patient.

10. The method of claim 1, further comprises terminating the delivery of the electrical stimulation prior to at least one of a subsequent contraction of the bladder or a subsequent contraction of the bowel.

11. A medical device system comprising:
a therapy module configured to deliver electrical stimulation therapy to a patient; and
a processor configured to initiate delivery of the electrical stimulation therapy with a frequency of approximately 500 hertz or greater to the patient via the therapy delivery module following at least one of a contraction of a bladder or a contraction of a bowel of a patient, wherein the electrical stimulation therapy is configured to at least one of inhibit contraction of the bladder following the contraction of the bladder or inhibit contraction of the bowel following contraction of the bowel.

12. The system of claim 11, wherein the processor is configured to initiate delivery of the electrical stimulation therapy with a frequency of 500 hertz or greater to the patient via the therapy delivery module.

13. The system of claim 11, wherein the processor is configured to initiate delivery of the electrical stimulation therapy with a frequency of 1000 hertz or greater to the patient via the therapy delivery module.

14. The system of claim 11, wherein the processor is configured to initiate delivery of the electrical stimulation therapy with the frequency of 500 hertz to 1000 hertz to the patient via the therapy delivery module.

15. The system of claim 11, wherein the processor is configured to detect a voiding event of the patient, and initiate, in response to detecting the voiding event of the patient, the delivery of the electrical stimulation therapy with the frequency of approximately 500 hertz or greater to the patient via the therapy delivery module.

16. The system of claim 11, wherein the processor is configured to sense at least one of a physiological marker of the patient or patient input, and initiate, in response to the sensing of the physiological marker, the delivery of the electrical stimulation therapy with the frequency of approximately 500 hertz or greater to the patient to the patient via the therapy delivery module.

17. The system of claim 16, wherein the physiological marker comprises at least one of bladder impedance, bladder pressure, bowel impedance, bowel pressure, pudendal afferent nerve activity, sacral afferent nerve activity, muscle activity, or motion of the patient.

18. The system of claim 11, wherein the electrical stimulation comprises a first electrical stimulation exhibiting a first frequency of approximately 500 hertz or greater, wherein the processor is configured to deliver, via the therapy delivery module, a second electrical stimulation therapy to the patient in combination with the first electrical stimulation therapy, and wherein the second electrical stimulation therapy exhibits a second frequency less than the first frequency.

19. The system of claim 11, wherein the processor is configured to detect the at least one of the contraction of the bladder or the contraction of the bowel of the patient, and initiate, in response to the detection of the at least one of the contraction of the bladder or the contraction of the bowel of the patient, the delivery of the electrical stimulation therapy with the frequency of approximately 500 hertz or greater to the patient via the therapy delivery module following the at least one of the contraction of the bladder or the contraction of the bowel of a patient.

20. The system of claim 11, wherein the processor is configured to terminate the delivery of the electrical stimulation prior to at least one of a subsequent contraction of the bladder or a subsequent contraction of the bowel.

* * * * *